United States Patent
Xu

(10) Patent No.: US 10,617,423 B2
(45) Date of Patent: Apr. 14, 2020

(54) METHOD FOR SETTING ELASTIC THREADS IN LIGATION DEVICE AND AUTOMATIC ELASTIC THREAD LIGATION DEVICE

(71) Applicant: Ruiyun Xu, Guangzhou (CN)

(72) Inventor: Ruiyun Xu, Guangzhou (CN)

( * ) Notice: Subject to any disclaimer, the term of this patent is extended or adjusted under 35 U.S.C. 154(b) by 484 days.

(21) Appl. No.: 15/021,700

(22) PCT Filed: Jul. 15, 2014

(86) PCT No.: PCT/CN2014/082223
§ 371 (c)(1),
(2) Date: Mar. 13, 2016

(87) PCT Pub. No.: WO2015/039488
PCT Pub. Date: Mar. 26, 2015

(65) Prior Publication Data
US 2016/0220258 A1    Aug. 4, 2016

(30) Foreign Application Priority Data
Sep. 18, 2013 (CN) .......................... 2013 1 0430853

(51) Int. Cl.
*A61B 17/12* (2006.01)
*A61B 90/00* (2016.01)
*A61B 17/30* (2006.01)

(52) U.S. Cl.
CPC ............... *A61B 17/12013* (2013.01); *A61B 2017/12018* (2013.01); *A61B 2017/306* (2013.01);
(Continued)

(58) Field of Classification Search
CPC .............. A61B 17/12; A61B 17/12009; A61B 17/12013; A61B 2017/12004;
(Continued)

(56) References Cited

U.S. PATENT DOCUMENTS

| | | | | |
|---|---|---|---|---|
| 5,957,936 A * | 9/1999 | Yoon | ................. | A61B 17/12013 606/144 |
| 6,730,101 B1 * | 5/2004 | Peifer | ............... | A61B 17/12013 606/139 |
| 2008/0082113 A1 * | 4/2008 | Bishop | ............. | A61B 17/06166 606/151 |

* cited by examiner

*Primary Examiner* — Katherine M Shi
*Assistant Examiner* — Lindsey Bachman
(74) *Attorney, Agent, or Firm* — JCIP Global Inc.

(57) ABSTRACT

The present invention provides a method for setting elastic threads in a ligation device and an automatic elastic thread ligation device using the method. At least one elastic thread (2) is arranged along the outer wall of a barrel (3) of the ligation device, and an annular sleeve (21) with an adjustable aperture and formed at the front end of the elastic thread (2) is sleeved on the outer wall of the front end of the barrel; a traction thread (26) on the ligation device is connected with the annular sleeve (21) of the elastic thread (2), and when the traction thread (26) is pulled, the traction thread drives the annular sleeve (21) to move towards the orifice of the barrel (3), until the annular sleeve is disengaged from the orifice; a force bearing part of the annular sleeve (21) at the front end of the elastic thread is propped forwards, meanwhile, the tail end of the elastic thread (2) is pulled backwards, and the countertraction between the two acting forces leads to a gradual decrease of the aperture of the annular sleeve (21) at the front end of the elastic thread (2). In the automatic elastic thread ligation device, rubber rings are replaced by the elastic threads, after the annular sleeve at the front end of the elastic thread is pulled by the traction thread and pops up from the orifice of the barrel, the aperture of the annular sleeve can be decreased gradually by pulling the tail end of the elastic thread until the aperture becomes approximately zero, so that tighter ligation of the target tissue can be achieved, and an ulcer surface is extremely small after the
(Continued)

target tissue becomes necrotic and falls off, so that the probability of postoperative bleeding is lowered.

20 Claims, 14 Drawing Sheets

(52) U.S. Cl.
CPC ............... *A61B 2090/0804* (2016.02); *A61B 2090/0811* (2016.02)

(58) Field of Classification Search
CPC .... A61B 2017/12018; A61B 17/32056; A61B 2017/0474
See application file for complete search history.

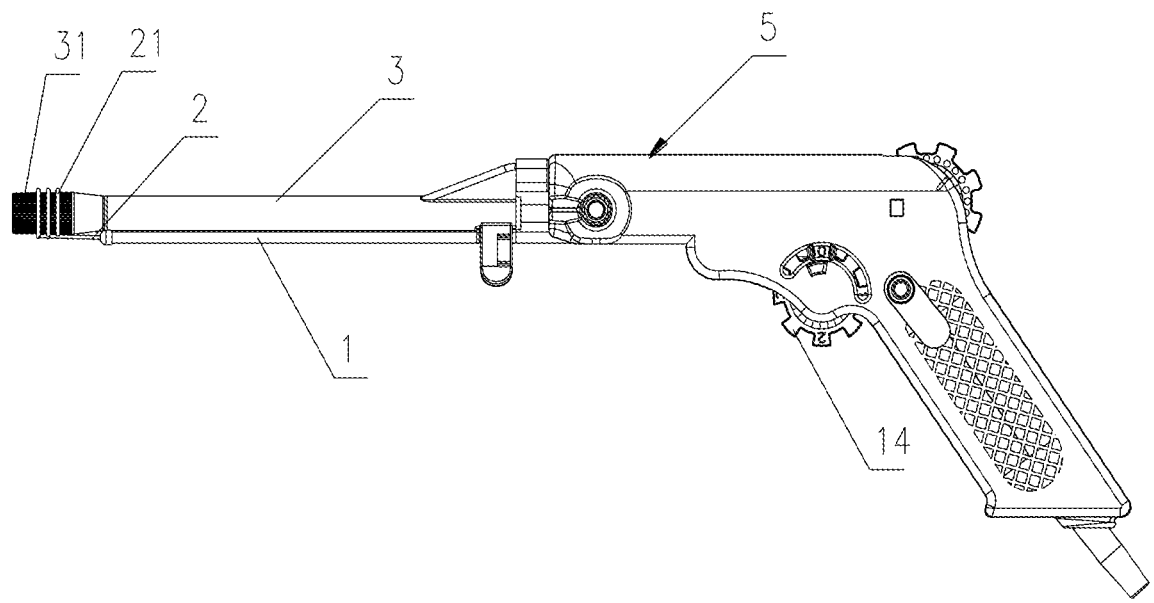
FIG. 19
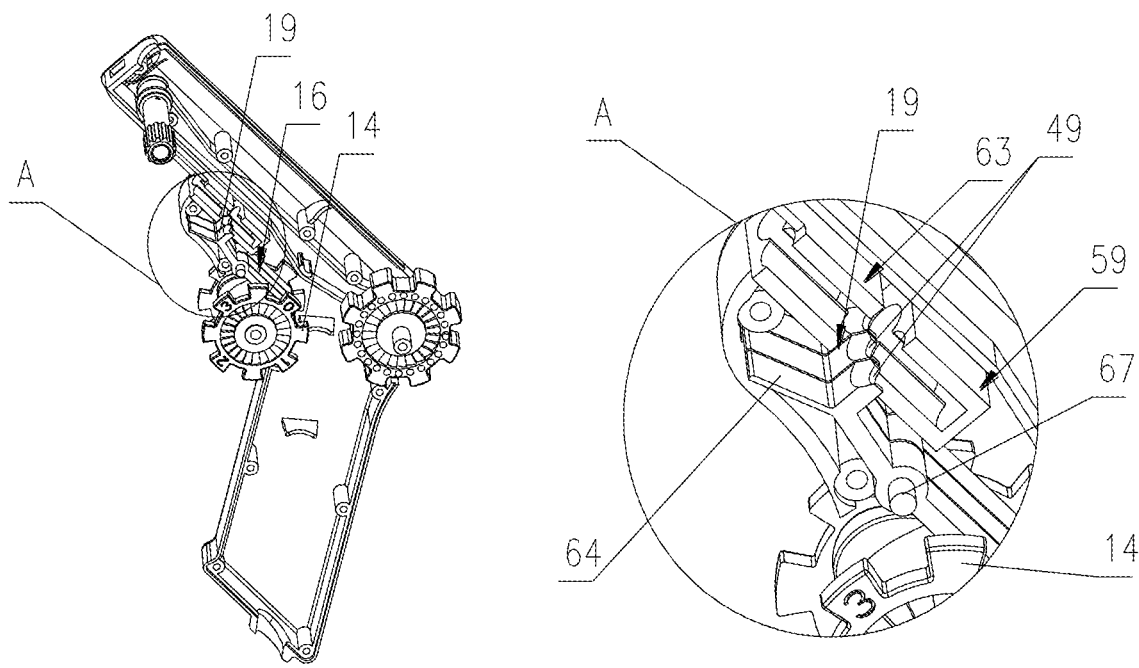
FIG. 20
FIG. 21

METHOD FOR SETTING ELASTIC THREADS IN LIGATION DEVICE AND AUTOMATIC ELASTIC THREAD LIGATION DEVICE

CROSS-REFERENCE TO RELATED APPLICATIONS

This application claims priority from PCT Application No. PCT/CN2014/082223, filed Jul. 15, 2014 and CN Application No. 201310430853.4, filed Sep. 18, 2013, the contents of which are incorporated herein in the entirety by reference.

FIELD OF THE INVENTION

The present invention relates to medical instrument technology, particularly relates to a method for setting elastic threads in a ligation device, and further relates to an automatic elastic thread ligation device using the method.

BACKGROUND OF THE INVENTION

"Ligation of hemorrhoids (also known as rubber ring ligation of hemorrhoids, suction ligation of hemorrhoids and the like)" is a common method for treating hemorrhoids, the curative effect is exact, the principle thereof is to ligate a specially-made rubber ring (such as a rubber ring, a latex ring, a silicone ring and the like) on the roots (or the substrates) of hemorrhoids, to block blood supply to the hemorrhoids via the elastic retractive force of the rubber ring to induce necrosis, atrophy and fall-off of the hemorrhoids, so as to fulfill a cure purpose. Traditional instruments used for carrying out the ligation surgery are extremely simple, time-consuming and laborious to operate and are prone to leading to complications. To change this situation, over the past decade, an automatic instrument, namely, an automatic hemorrhoids ligation device (also known as a repeating hemorrhoids ligation device, a repeating hemorrhoids suction ligation device and the like), has been proposed to make the ligation surgery be simple and easy. The advantages of using the instrument to perform the ligation surgery are as follows: the operation is simple, convenient, fast and accurate; a single person can finish the surgery, and only 5-10 minutes are taken; the probability of complications is lower; patients generally need no anesthesia, and the pain is mild; most patients do not need to be hospitalized, so that the treatment cost is low.

The Chinese authorized utility model patents (ZL200820051521.X) discloses a repeating hemorrhoids suction ligation device, including a body, as well as a pipe body arranged at the front end of the body, a plurality of stretched rubber rings which are sleeved on the pipe body in sequence, a negative pressure suction joint arranged behind the pipe body and communicated with the inner cavity of the pipe body and a rubber ring popup device arranged on the body, wherein an emission head communicated with the inner cavity of the pipe body is sleeved on the front end of the pipe body, and the rubber rings are sleeved on the emission head; the rubber ring popup device includes at least one traction thread and a winding device arranged in the body, the front end of the traction thread is winded on the winding device; the tail end of the traction thread penetrates through the interior of the pipe body, is folded back from the orifice of the emission head and is connected with the rubber rings along the outer wall of the emission head through a traction mechanism.

The above-mentioned hemorrhoids suction ligation device (also known as a hemorrhoids ligation device) and other types of hemorrhoids ligation devices at home and abroad have a common feature, that is, "rubber rings" are used as basic materials which are ligated on the roots of hemorrhoids; available raw materials for making the rubber rings include natural rubber, latex or silica gel, etc.

The clinical efficacy of the rubber ring ligation of hemorrhoids is directly related to two technical indicators, namely, "internal aperture of the rubber ring" and "the elastic retractive force of the rubber ring". The use of the rubber ring as the ligation material has some inherent disadvantages: (1) due to the inherent characteristics of the natural rubber (or latex or silica gel and the like), the internal aperture of the rubber ring cannot be infinitely small, and the rubber ring can be generally only made to 2.0-2.5 mm (at least not less than 1.5 mm), otherwise the rubber ring is easy to break when being stretched in a ligation process. This means that within the size range of the diameter of 2.0-2.5 mm (at least not less than 1.5 mm), the ligated hemorrhoids tissues are applied with no elastic retractive force, and finally, ulcer formed after tissue necrosis and fall-off ranges for about 2.0-2.5 mm (at least not less than 1.5 mm); (2) when the rubber rings are installed on the ligation device at a stretched state, the rubber rings are liable to fatigue gradually with time to increase the internal aperture; and (3) due to the influence of such factors as climate and environment and the like, the rubber rings are easy to age over time, so that the elastic retractive force becomes weaker.

Due to the influence of the above factors, the following consequences will be generated possibly: (1) rubber ring slippage occurs within a short period after the surgery, resulting in treatment failure; (2) postoperative bleeding complications are generated (according to statistics, the postoperative bleeding rate of the rubber ring ligation of hemorrhoids is 2-5%); and (3) hemorrhoids block necrosis is incomplete, healing of the ulcer surface is delayed and the efficacy is influenced.

SUMMARY OF THE INVENTION

One purpose of the present invention is to provide a method for setting elastic threads in a ligation device, which can be used for conveniently adjusting the popup and tightening of elastic threads.

The above purpose of the present invention is achieved by the following technical measures: a method for setting elastic threads in a ligation device, wherein at least one elastic thread is arranged along the outer wall of a barrel of the ligation device, and an annular sleeve with an adjustable aperture and formed at the front end of the elastic thread is sleeved on the outer wall of the front end of the barrel; a traction thread on the ligation device is connected with the annular sleeve of the elastic thread, and when the traction thread is pulled, the traction thread drives the annular sleeve to move towards the orifice of the barrel until the annular sleeve is disengaged from the orifice; a force bearing part of the annular sleeve at the front end of the elastic thread is propped forwards, meanwhile, the tail end of the elastic thread is pulled backwards, and countertraction between the two acting forces leads to a gradual decrease of the aperture of the annular sleeve at the front end of the elastic thread.

In the present invention, rubber rings are replaced by the elastic threads, after the annular sleeve at the front end of the elastic thread is pulled by the traction thread and pops up from the orifice of the barrel, the aperture of the annular sleeve can be decreased gradually by pulling the tail end of the elastic thread until the aperture becomes approximately zero, and thus the aperture of the annular sleeve of the elastic thread can be effectively adjusted.

According to the present invention, the annular sleeve with the adjustable aperture and at the front end of the elastic thread is formed by knotting a slipknot, and the knotting point of the annular sleeve is the force bearing part propping against the annular sleeve; or the annular sleeve with the adjustable aperture and at the front end of the elastic thread is formed by penetrating a thread fixing bead through the elastic thread, and the thread fixing bead is the force bearing part propping against the annular sleeve.

As an embodiment of the present invention, a thread ejector sleeve is arranged on the elastic thread, and after the tail end of the elastic thread penetrates through the thread ejector sleeve, the tail end of the elastic thread is buckled with the orifice at the rear end of the thread ejector sleeve; a force is applied to the thread ejector sleeve, to prop the orifice at the front end thereof against the force bearing part of the annular sleeve, meanwhile, the tail end of the elastic thread is pulled backwards, and the countertraction between the two forces leads to the gradual decrease of the aperture of the annular sleeve.

According to the present invention, a neck is formed in the tail end of the thread ejector sleeve, and a shiftable clamping projection is arranged in the neck to position the thread ejector sleeve.

Another purpose of the present invention is to provide an automatic elastic thread ligation device. The ligation device replaces the ligation rubber rings in the prior art with elastic threads, and the ligation apertures of the elastic threads can be effectively adjusted.

The above purpose of the present invention is achieved by the following technical solutions: an automatic elastic thread ligation device includes a barrel, a gun body and a traction thread, wherein the traction thread penetrates through the barrel and the rear end thereof is positioned in the gun body, the front end of the traction thread is folded back on the outer wall of the front end of the barrel after stretching out from the barrel; wherein the automatic elastic thread ligation device further includes at least one elastic thread, the elastic thread is arranged along the outer wall of the barrel, an annular sleeve with an adjustable aperture and formed at the front end of the elastic thread is sleeved on the outer wall of the front end of the barrel, and the annular sleeve is connected with the front end of the traction thread; when the traction thread is pulled backwards, the traction thread drives the annular sleeve to move towards the orifice of the barrel until the annular sleeve is disengaged from the orifice; a force bearing part of the annular sleeve at the front end of the elastic thread is propped forwards, meanwhile, the tail end of the elastic thread is pulled backwards, and countertraction between the two forces leads to a gradual decrease of the aperture of the annular sleeve.

According to the present invention, the traction thread pulls the annular sleeve to sleeve the same on a target tissue, and since the aperture of the annular sleeve can be gradually decreased, tighter ligation of the target tissue can be achieved; the ulcer surface is extremely small after the target tissue becomes necrotic and falls off, so that the probability of postoperative bleeding is reduced, and meanwhile, other inherent disadvantages of the aforementioned rubber ring ligation surgery are avoided, for example, rubber ring slippage occurs after a short period to result in treatment failure, and hemorrhoids block necrosis is incomplete to delay the healing of the ulcer surface, etc.

The automatic elastic thread ligation device provided by the present invention further includes a thread ejector sleeve used for propping against the force bearing part, one thread ejector sleeve is sleeved on each elastic thread, the tail end of the elastic thread penetrates through the thread ejector sleeve and is buckled with the orifice at the rear end of the thread ejector sleeve, and the rear of the thread ejector sleeve is inserted into the gun body.

As an embodiment of the present invention, the rear of the thread ejector sleeve is inserted into the gun body through a thread ejector sleeve release mechanism, the thread ejector sleeve release mechanism includes a slide rail and a thread ejector sleeve release button, wherein the slide rail is transversely arranged on the inner wall of the gun body along the inner cavity of the gun body, the thread ejector sleeve release button is slidably installed on the slide rail, and the thread ejector sleeve release button is exposed on the side face of the gun body, a clamping projection is arranged on the thread ejector sleeve release button, a neck is formed in the rear of the thread ejector sleeve, and the clamping projection is clamped in the neck to position the thread ejector sleeve.

According to the present invention, the thread ejector sleeve release button is integrally made from a press panel, a rectangular elastic arm and a slide block, wherein one end of the slide block and the one end of the elastic arm are respectively connected to the back surface of the press panel, and the slide block is located above the elastic arm, the slide block is slidably installed on the slide rail, the clamping projection is located on the top face of the slide block, the neck of the thread ejector sleeve corresponds to the clamping projection downwards, the other end of the elastic arm is used as the lower end of the elastic arm to be propped on the inner wall of the gun body, the original length of the elastic arm is larger than the length of the slide block, and the press panel is located on the side face of the gun body for receiving a press force.

As another embodiment of the present invention, the rear of the thread ejector sleeve is inserted into the gun body through a thread ejector sleeve popup mechanism, the thread ejector sleeve popup mechanism includes a thread ejector sleeve release wheel and at least one strip-shaped thread ejector sleeve limiting plate, one thread ejector sleeve is correspondingly clamped and limited at the front end part of each thread ejector sleeve limiting plate, all the thread ejector sleeve limiting plates are arranged in parallel along the longitudinal direction and are collectively hinged on the inner wall of the gun body via the middle part; at least one projection used for prizing the thread ejector sleeve limiting plate is alternately distributed on the circumferential wheel surface of the thread ejector sleeve release wheel, the rotation of each projection with the thread ejector sleeve release wheel corresponds to one thread ejector sleeve limiting plate located above the wheel surface, the thread ejector sleeve release wheel is rotated to enable the projection to lift the rear end part of the corresponding thread ejector sleeve limiting plate, so as to drive the thread ejector sleeve limiting plate to rotate around a hinge shaft thereof, the front end part of the thread ejector sleeve limiting plate drops off to withdraw the limit on the thread ejector sleeve, and the thread ejector sleeve pops up under the restoring force of the elastic thread.

The above-mentioned thread ejector sleeve popup mechanism is composed of few parts and components, and the parts and components are simple in structures and low in manufacturing costs; necks with different positions do not need to be arranged on each thread ejector sleeve, thereby lowering the manufacturing difficulty; moreover, when popping out the thread ejector sleeve, the thread ejector sleeve release wheel is rotated to enable the projection thereon to lift the thread ejector sleeve limiting plate, so as to withdraw the limit on the thread ejector sleeve, and the acting force applied to the thread ejector sleeve release wheel will not influence the holding stability, therefore the operation is convenient.

According to the present invention, a fixture block is arranged at the front end part of the thread ejector sleeve limiting plate, a clamping joint connected with the tail end of the elastic thread is inserted into the orifice at the rear end of the thread ejector sleeve, a limiting groove is formed on the clamping joint, and the fixture block is clamped in the limiting groove.

As an embodiment of the present invention, the clamping joint is mainly composed of a columnar inner segment inserted into the orifice at the rear end of the thread ejector sleeve and an outer segment stretching out from the thread ejector sleeve, the limiting groove is annularly formed in the spindle-shaped outer segment, a neck is formed in the upper end of the fixture block, the notch of the neck is upward, the outline thereof is applicable to the outline of the bottom of the limiting groove, and the neck is clamped in the limiting groove.

To improve the installation stability of the thread ejector sleeve, as an improvement of the present invention, the thread ejector sleeve popup mechanism of the automatic elastic thread ligation device further includes a rear supporting seat used for being inserted into the outer segment of the clamping joint and a front supporting seat used for guiding the thread ejector sleeve to install the same in the gun body of the ligation device, the rear of the thread ejector sleeve stretches into the rear supporting seat after penetrating through the front supporting seat, and the fixture block is clamped in the limiting groove on the front side of the rear supporting seat.

As a further improvement of the present invention, an elastic arm obliquely extends from the lower side of the fixture block at the front end part of the thread ejector sleeve limiting plate, the front end of the elastic arm is propped on a supporting column for providing an upward acting force to jack the fixture block of the thread ejector sleeve limiting plate in the limiting groove of the clamping joint and resetting the prized projection of the thread ejector sleeve limiting plate at the same time.

According to the present invention, a marker used for marking the thread ejector sleeve is arranged on the circumference of the side face of the thread ejector sleeve release wheel, and the position of the marker corresponds to that of the projection to master the popup condition of the thread ejector sleeve.

Further, the automatic elastic thread ligation device provided by the present invention further includes a reel, the reel is arranged at the rear in the gun body, and the rear end of the traction thread is winded on the reel for positioning the rear end of the traction thread.

According to the present invention, the front end of the traction thread is located between the outer wall of the barrel and the annular sleeve, a traction block is arranged on the front end of the traction thread, and the traction block is located behind the annular sleeve for clamping the annular sleeve to connect the traction thread with the annular sleeve.

As a further improvement of the present invention, an emission head is installed at the front end of the barrel in the present invention, and the annular sleeve of the elastic thread is sleeved on the outer wall of the emission head; the traction thread is composed of a main traction thread and at least two branch traction threads, which are interconnected, the other end of the main traction thread is winded on the reel, the other end of each branch traction thread is folded back on the outer wall of the emission head after stretching out from the orifice of the emission head, and the branch traction threads are symmetrically distributed along the orifice of the emission head to provide a uniform tension to the annular sleeve of the elastic thread.

According to the present invention, the elastic thread is formed by wrapping an elastic strip (an inner layer) with a netty woven layer (an outer layer), both are made from a high molecular material, and the netty woven layer can expand with the stretching of the elastic strip. This special double-layer structure of the elastic thread not only ensures good elasticity, but also can bear strong axial tension without breaking, and when being sleeved on the target tissue, the annular sleeve of the elastic thread at the stretched state can be further tightened to decrease the aperture; in addition, the elastic thread is unlikely to age and fatigue, so that the service life is long, and the ligation effect can be improved.

As an embodiment of the present invention, the barrel is detachably inserted onto the gun body, the rear end of the traction thread is connected to a driving wheel located at the rear of the gun body through a transfer transmission mechanism, and the transfer transmission mechanism is driven by the driving wheel to pull the traction thread backwards.

According to the present invention, the transfer transmission mechanism includes a traction thread turn button, a transfer shaft and a transmission belt, wherein the transfer shaft is transversely arranged at the front end in the gun body 5 along the transverse direction, one end of the transmission belt is winded on the driving wheel, the other end of the transmission belt is sleeved on the inner end of the transfer shaft, the traction thread turn button is sleeved on the outer end of the transfer shaft, the traction thread turn button is engaged with the sleeving position of the transfer shaft, the rear end of the traction thread is winded on the traction thread turn button, the driving wheel is shifted to drive the transfer shaft to rotate through the transmission belt, so that the traction thread turn button rotates for winding the thread to pull the traction thread backwards, so as to drive the annular sleeve to move towards the orifice of the barrel until the annular sleeve is disengaged from the orifice.

Further, the automatic elastic thread ligation device provided by the present invention further includes a buckling structure which is arranged on the outer wall of the barrel for fixing the thread ejector sleeve, the thread ejector sleeve is arranged along the outer wall of the barrel, and the rear of the thread ejector sleeve is installed in the gun body through a detachable structure; the elastic thread penetrates through the thread ejector sleeve, and the tail end thereof is buckled with the orifice of the rear end of the thread ejector sleeve; the buckling structure is composed of a thread ejector sleeve fixing clip and at least one groove formed in the outer wall of the barrel, the thread ejector sleeve fixing clip is H-shaped, namely, the thread ejector sleeve fixing clip is composed of a transverse plate and a pair of vertical plates, the upper plate surface of the transverse plate is provided with at least one bayonet, and the groove corresponds to the bayonet up and down; necks are formed in both sides of the groove, a clamping hook is arranged at the upper end of the side plate of the thread ejector sleeve fixing clip, the clamping hook is clamped in the necks to install the thread ejector sleeve fixing clip on the barrel, and the groove and the bayonet are oppositely closed to clamp the thread ejector sleeve so as to fix the thread ejector sleeve before the barrel is installed on the gun body.

As an improvement of the present invention, a C-shaped clamping opening is formed in the outer wall of one vertical plate of the thread ejector sleeve fixing clip, the opening of the C-shaped clamping opening is outward, and the traction thread turn button is embedded into the C-shaped clamping opening from the opening to be clamped, so as to fix the traction thread turn button before the barrel is installed on the gun body.

According to the present invention, two upper and lower parallel through holes are formed in the rear end of the barrel, the through hole at the upper side is a tubular plug, one end of a negative pressure pipeline in the gun body stretches out from the front end of the gun body and is provided with a socket, and the plug is hermetically inserted into the socket to communicate the barrel with the negative pressure pipeline; the through hole at the lower side is sealed by a rubber plug, a minipore for enabling the traction thread to pass through is formed in the rubber plug, a wiring groove communicated with an open bore enabling the traction thread turn button to penetrate through is formed in the front end of the gun body, and the traction thread penetrates through the minipore of the rubber plug and extends straightly along the wiring groove to be winded on the traction thread turn button.

As an embodiment of the present invention, a fixture block with a clamping hook is arranged at the rear end of the barrel in the present invention, a clamping hole and a pushing element are arranged at the front end of the gun body, the clamping hook of the fixture block is clamped in the clamping hole, the pushing element is located in an open pore, the pushing element is composed of an elastic arm and a push block connected to the lower end of the elastic arm, the upper end of the elastic arm is connected to the upper edge of the open pore to provide a restoring force to the push block, the push block corresponds to the clamping hook of the fixture block, and the push block is pushed towards the interior of the gun body to enable the push block to shift the clamping hook to deviate the clamping hook from the clamping hole, so as to detachably insert the barrel assembly onto the gun body.

As a further improvement of the present invention, a tensioning column used for tensioning the transmission belt is arranged on the inner wall of the gun body, the tensioning columns are distributed on the peripheral side of the transmission belt, and the tensioning column supports the transmission belt to stably transmit power.

The present invention further provides a thread ejector sleeve popup mechanism used in the above-mentioned automatic elastic thread ligation device, including at least one thread ejector sleeve sleeved on an elastic thread at a stretched state, a thread ejector sleeve release wheel and at least one strip-shaped thread ejector sleeve limiting plate, wherein one thread ejector sleeve is correspondingly clamped and limited at the front end part of each thread ejector sleeve limiting plate, all the thread ejector sleeve limiting plates are arranged in parallel along the longitudinal direction and are collectively hinged on the inner wall of the gun body via the middle part; at least one projection used for prizing the thread ejector sleeve limiting plate is alternately distributed on the circumferential wheel surface of the thread ejector sleeve release wheel, the rotation of each projection with the thread ejector sleeve release wheel corresponds to one thread ejector sleeve limiting plate located above the wheel surface, the thread ejector sleeve release wheel is rotated to enable the projection to lift the rear end part of the corresponding thread ejector sleeve limiting plate, so as to drive the thread ejector sleeve limiting plate to rotate around a hinge shaft thereof, the front end part of the thread ejector sleeve limiting plate drops off to withdraw the limit on the thread ejector sleeve, and the thread ejector sleeve pops up under the restoring force of the elastic thread.

The present invention further provides a barrel assembly used in the automatic elastic thread ligation device, including a barrel, a traction thread, a traction thread turn button, an elastic thread, a thread ejector sleeve and a thread ejector sleeve fixing clip, wherein the rear end of the traction thread penetrates through the rear end port of the barrel and is winded on the traction thread turn button, the front end of the traction thread is folded back on the outer wall of the front end of the barrel after stretching out from the front end port of the barrel; at least one elastic thread is arranged, the elastic thread is arranged along the outer wall of the barrel, an annular sleeve with an adjustable aperture and formed at the front end of the elastic thread is sleeved on the outer wall of the front end of the barrel, and the annular sleeve is connected with the front end of the traction thread; the thread ejector sleeve is arranged on each elastic thread, and the tail end of the elastic thread penetrates through the thread ejector sleeve and is buckled with the orifice at the rear end of the thread ejector sleeve; each thread ejector sleeve is clamped on the barrel through the fixing clip, and the traction thread turn button is clamped on the fixing clip.

Compared with the prior art, the present invention has the following significant advantages in specific use:

(1) According to the present invention, after the annular sleeve at the front end of the elastic thread is sleeved on the target tissue, the aperture of the annular sleeve can be gradually decreased (can be approximately zero) by tightening the elastic thread, so tighter ligation of the target tissue can be achieved, the ulcer surface is extremely small after the target tissue becomes necrotic and falls off, so that the probability of postoperative bleeding is lowered, and meanwhile, other inherent disadvantages (for example, rubber ring slippage occurs after a short period to result in treatment failure, and hemorrhoids block necrosis is incomplete to delay the healing of the ulcer surface, and the like) of the aforementioned rubber ring ligation surgery are avoided.

(2) Since the ligation is extremely tight, and will not slip, so sites ligated on an intestinal wall on the same horizontal plane can be increased (6-8 sites can be ligated, while only 3-4 sites are generally ligated in any previous ligation method), which greatly improves the effect of lifting an anal pad (or lifting a dropped mucous membrane of rectum).

(3) The elastic thread is unlikely to age and fatigue, so that the service life is long, and the ligation effect can be improved.

(4) The barrel, and the thread ejector sleeve, the thread ejector sleeve fixing clip, the traction thread turn button, the elastic thread and the traction thread and the like, which are arranged on the barrel can be combined and assembled to a barrel assembly capable of deviating from the gun body, these barrel assemblies can be conveniently and detachably installed on the gun body as a whole through the barrel, one gun body can be collectively used with a plurality of barrel assemblies, so that the number of hemorrhoids available for ligation is increased, when hemorrhoids exceeding the number of the elastic threads arranged on one barrel assembly need to be ligated, only the barrel assembly needs to be replaced instead of replacing the entire ligation device, so that the economic costs of patients are lowered.

(5) In the present invention, the branch traction threads are symmetrically distributed along the orifice of the emission head, so that a uniform tension can be provided for the elastic thread, and the annular sleeve can be smoothly sleeved on the target tissue.

(6) The automatic elastic thread ligation device provided by the present invention is simple, convenient, time-saving, labor-saving, strong in practicability, and is not only suitable for treating hemorrhoids, but also can be stretched in vivo to treat rectal prolapse, rectal polyp or other applicable anorectal diseases.

(7) The thread ejector sleeve popup mechanism is adopted in the present invention, when popping up the thread ejector sleeve, the thread ejector sleeve release wheel is rotated to enable the projection thereon to lift the thread ejector sleeve limiting plate, so as to withdraw the limit on the thread ejector sleeve, and the acting force applied to the thread ejector sleeve release wheel will not influence the holding stability, therefore the operation is convenient.

BRIEF DESCRIPTION OF THE DRAWINGS

A further detailed illustration of the present invention will be given below in combination with accompanying drawings and specific embodiments.

FIG. 19 is a schematic diagram of a structure of an automatic elastic thread ligation device in embodiment 3 of the present invention;

FIG. 20 is a first schematic diagram (no thread ejector sleeve is inserted) of a stereostructure of a thread ejector sleeve popup mechanism in embodiment 3 of the present invention;

FIG. 21 is an A partial enlarged schematic diagram in FIG. 20;

DETAILED DESCRIPTION OF PARTICULAR EMBODIMENTS OF THE INVENTION

Embodiment 1

Figure 1:
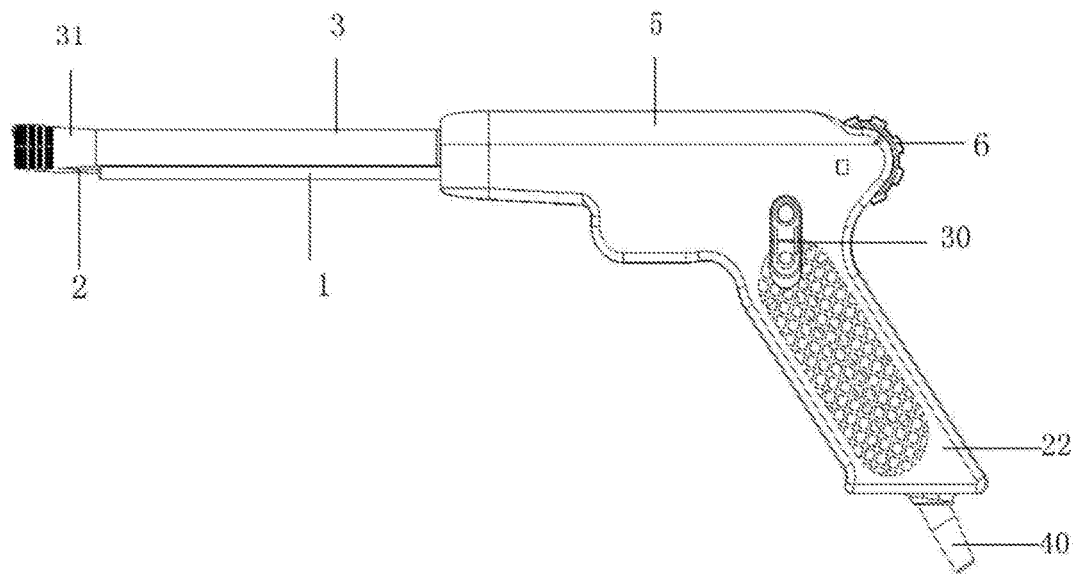
FIG. 1 is a first front view of embodiment 1 of the present invention.
Figure 2:
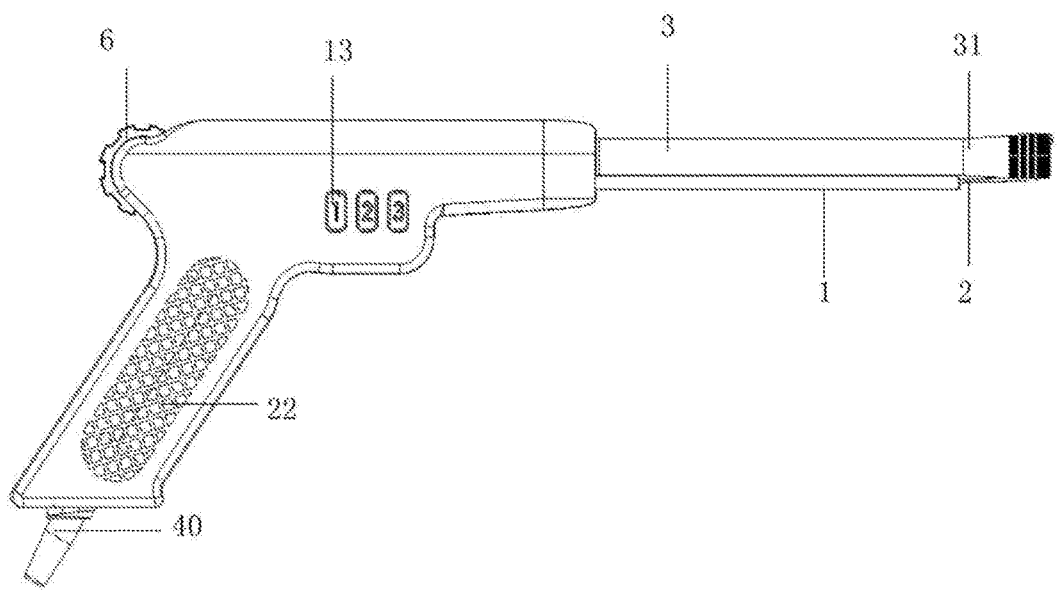
FIG. 2 is a second front view of embodiment 1 of the present invention.
Figure 3:
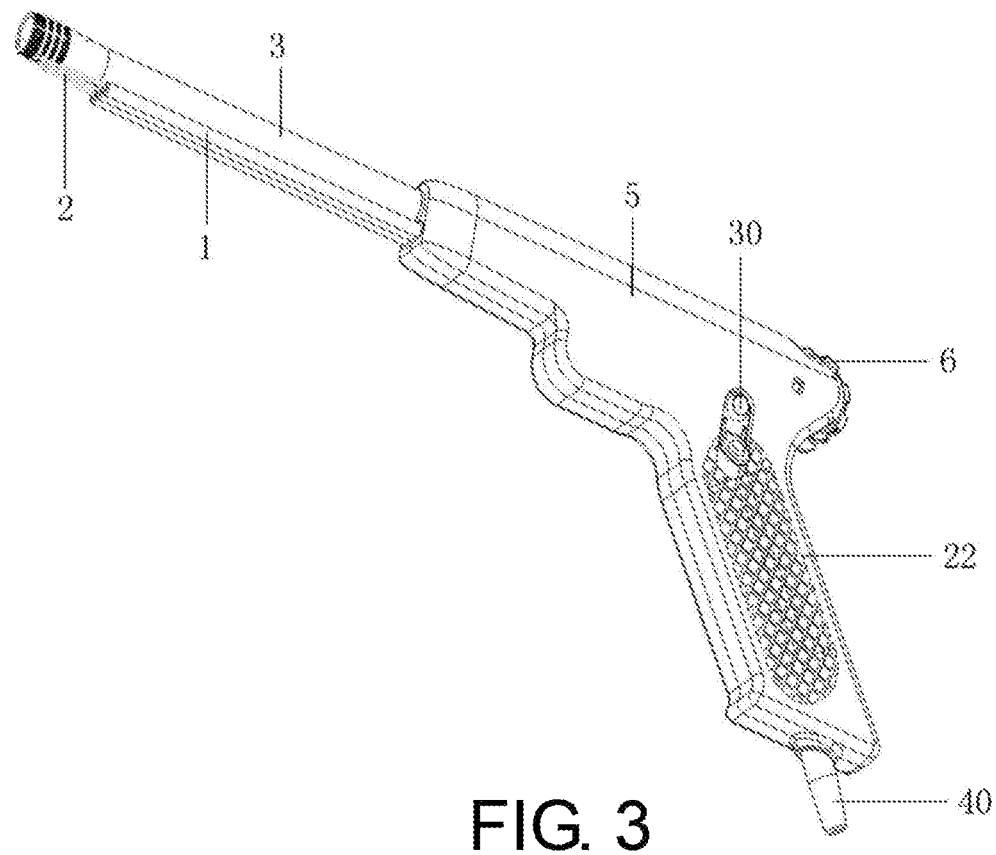
FIG. 3 is a schematic diagram of a stereostructure of embodiment 1 of the present invention.
Figure 4:
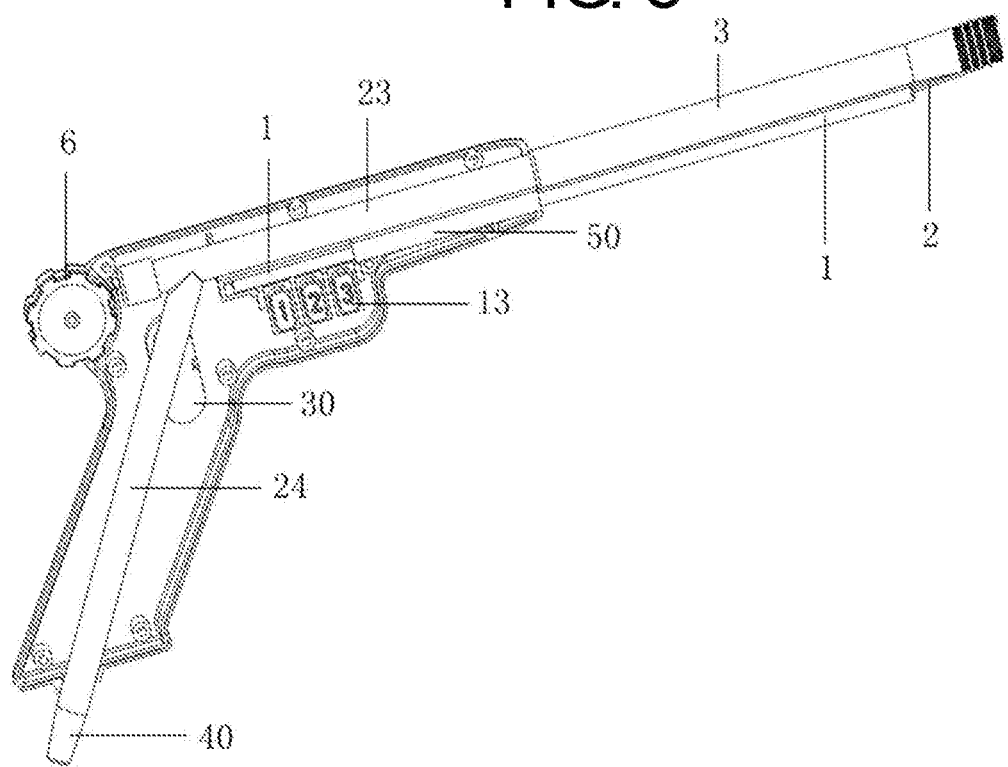
FIG. 4 is a schematic diagram of an overall structure of embodiment 1 of the present invention, after a gun body and a half shell of a stock are detached.
Figure 5:
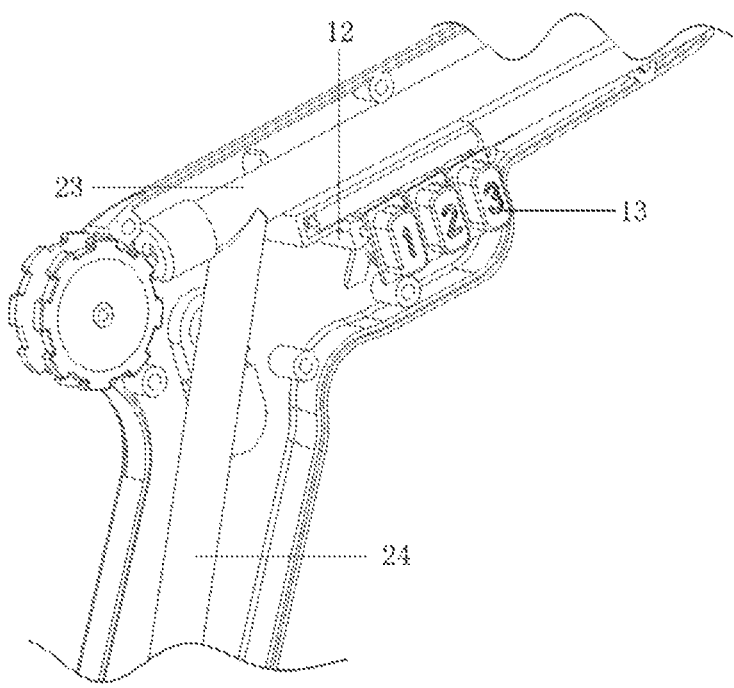
FIG. 5 is a schematic diagram of a partial structure of embodiment 1 of the present invention, after the gun body and the half shell of the stock are detached.
Figure 6:
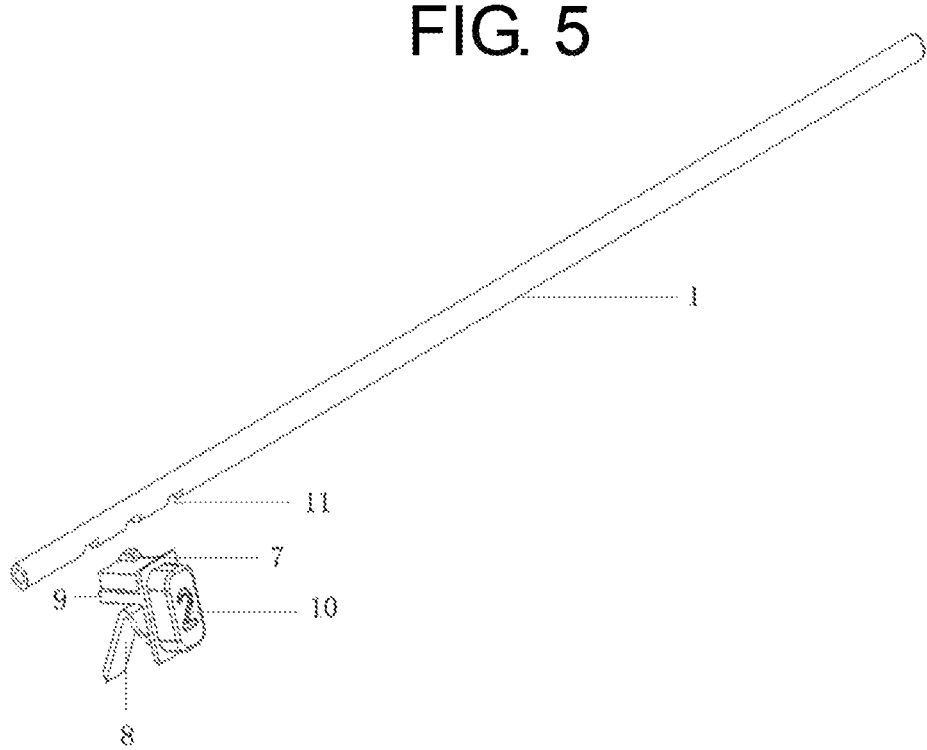
FIG. 6 is a schematic diagram of cooperation of a thread ejector sleeve and a thread ejector sleeve release button in embodiment 1.
Figure 7:
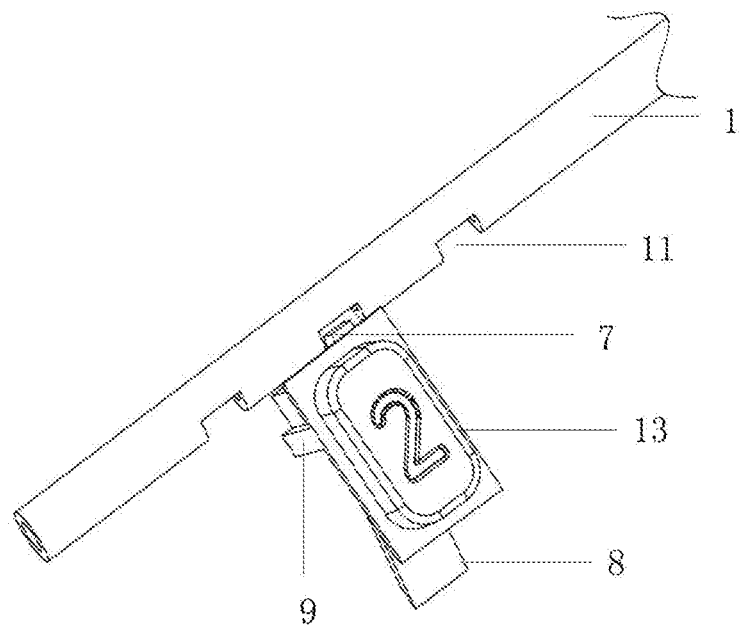
FIG. 7 is a schematic diagram of clamping a clamping projection on the thread ejector sleeve release button in a neck of the thread ejector sleeve in embodiment 1.
Figure 8:
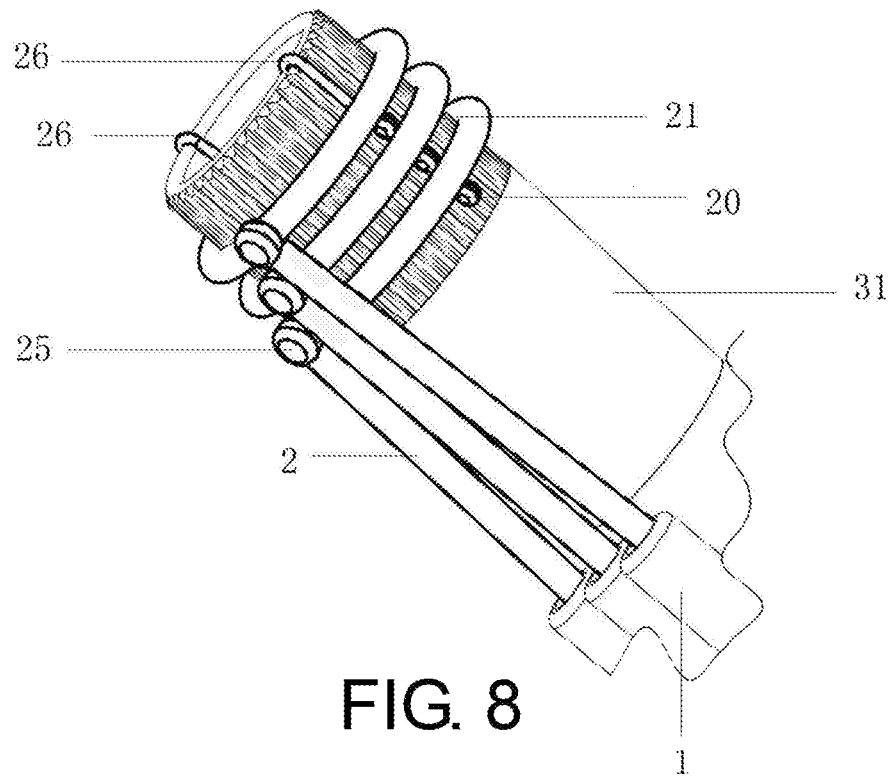
FIG. 8 is a schematic diagram of a partial structure of embodiment 1 of the present invention.
Figure 9:
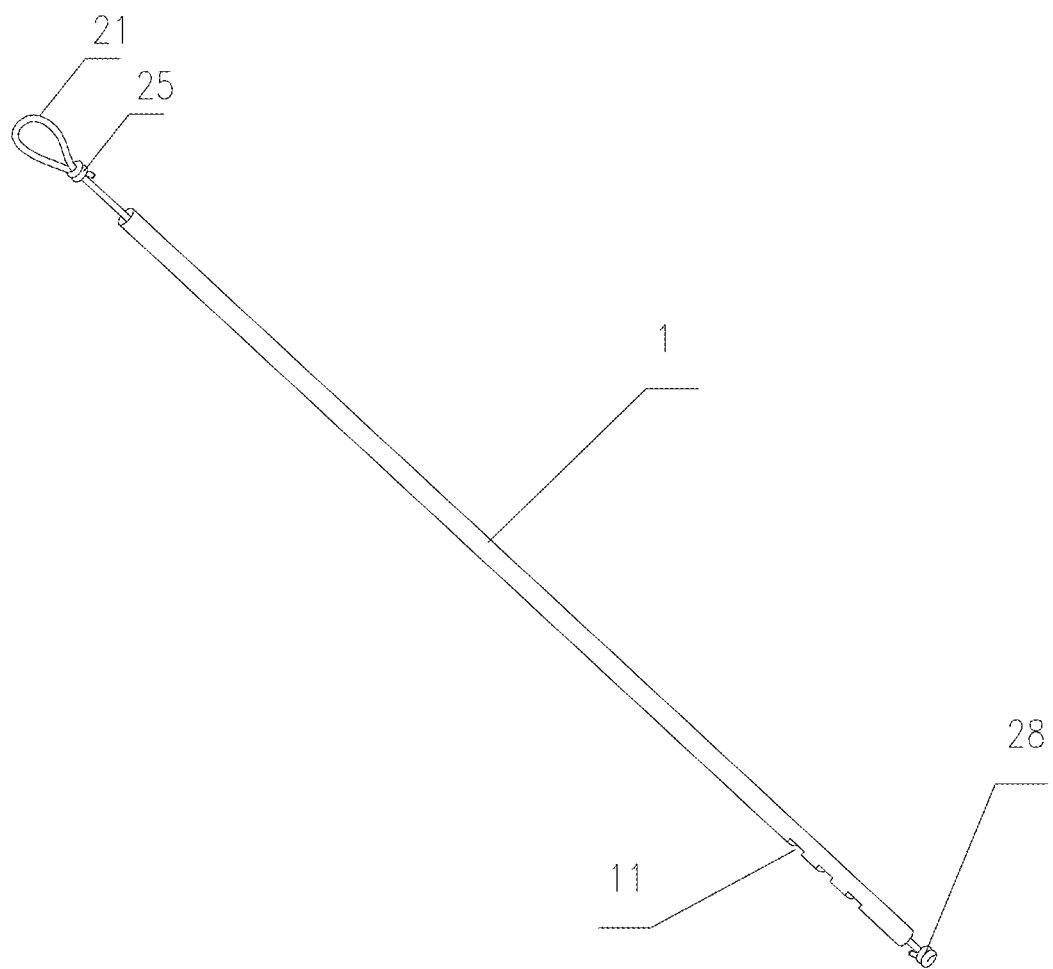
FIG. 9 is a schematic diagram of assembly of an elastic thread and the thread ejector sleeve in embodiment 1.

According to a method for setting elastic threads in a ligation device as shown in FIG. 1 to FIG. 9, at least one elastic thread is arranged along the outer wall of a barrel 3 of the ligation device, three elastic threads are arranged in the embodiment, a thread ejector sleeve 1 is sleeved on each elastic thread 2, the tail end of the elastic thread 2 penetrates through the thread ejector sleeve 1 and is knotted to a knot 28, and the tail end thereof is buckled with the orifice at the rear end of the thread ejector sleeve 1, an annular sleeve 21 with an adjustable aperture and formed at the front end of the elastic thread 2 is sleeved on the outer wall of the front end of the barrel 3, and at this time, the elastic thread 2 is at a stretched state; a traction thread on the ligation device penetrates through the barrel, the front end of the traction thread is folded back on the outer pipe wall of the front end of the barrel after stretching out from the barrel, and the rear end of the traction thread is positioned on a corresponding structure; a traction block is arranged on the front end of the traction thread and is located behind the annular sleeve 21, and the traction block is clamped with the annular sleeve for achieving the connection and linkage of the traction thread and the annular sleeve; in the embodiment, the traction block is the knot 20 formed by the traction thread per se. The annular sleeve 21 is formed by knotting one end of the elastic thread into an adjustable slipknot 25 in a conventional method, the knotting point of the annular sleeve is a force bearing part propping against the annular sleeve, and when the traction thread is pulled, the traction thread drives the annular sleeve to move towards the orifice of the barrel until the annular sleeve is disengaged from the orifice; a force is applied to the thread ejector sleeve to prop the orifice at the front end of the thread ejector sleeve against the knotting point of the annular sleeve, meanwhile the tail end of the elastic thread is pulled backwards, and the counter-traction between the two acting forces enables a gradual decrease of the aperture of the annular sleeve at the front end of the elastic thread.

Figure 10:
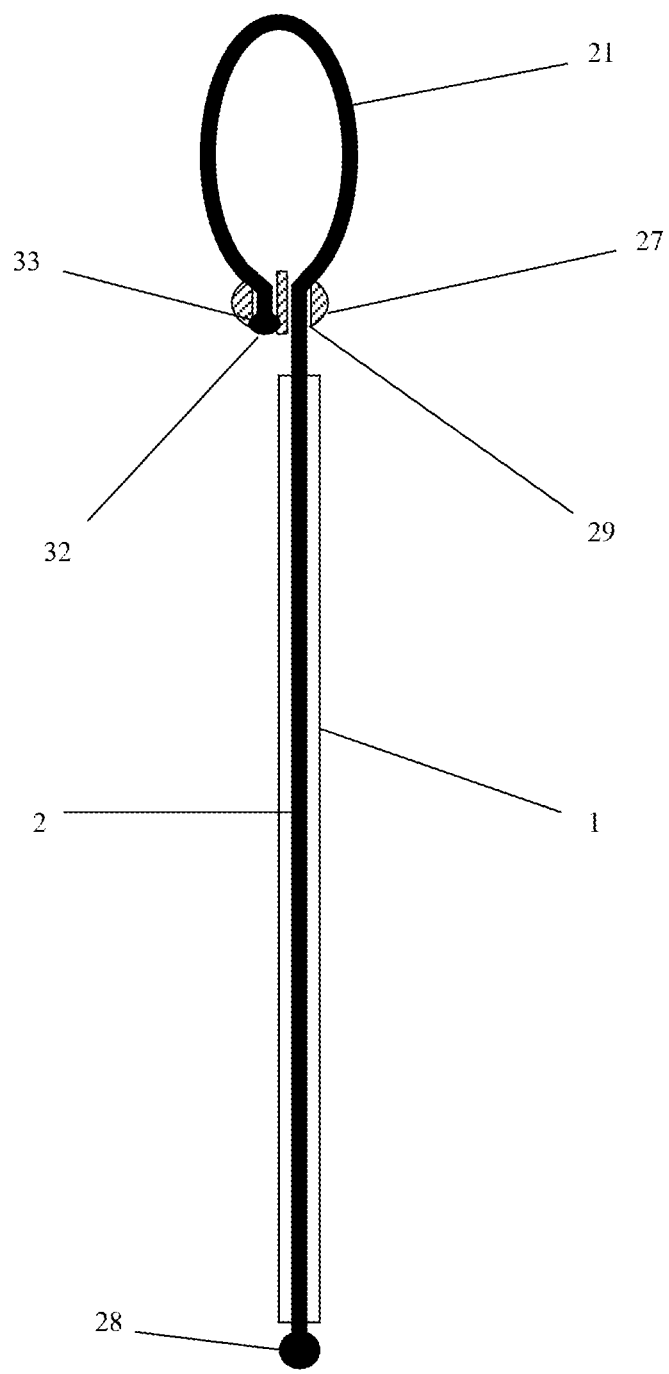
FIG. 10 is a schematic diagram of respectively penetrating the elastic thread through the thread ejector sleeve and a thread fixing bead to form an annular sleeve in embodiment 1.
Figure 11:
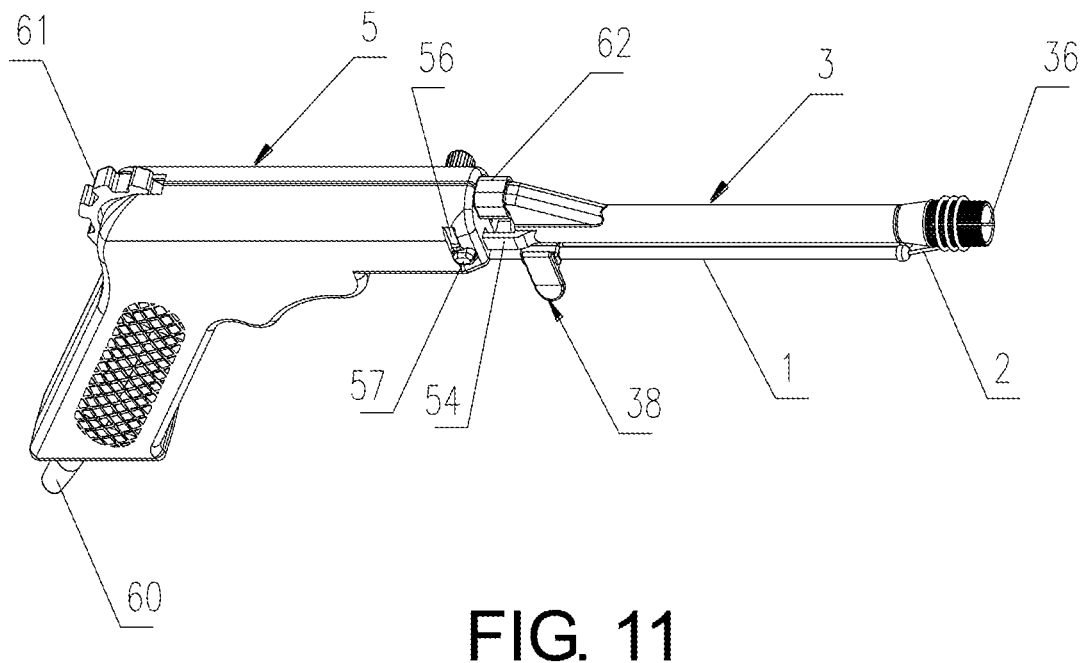
FIG. 11 is a schematic diagram (a back surface is displayed) of an overall structure of embodiment 2 of the present invention.
Figure 12:
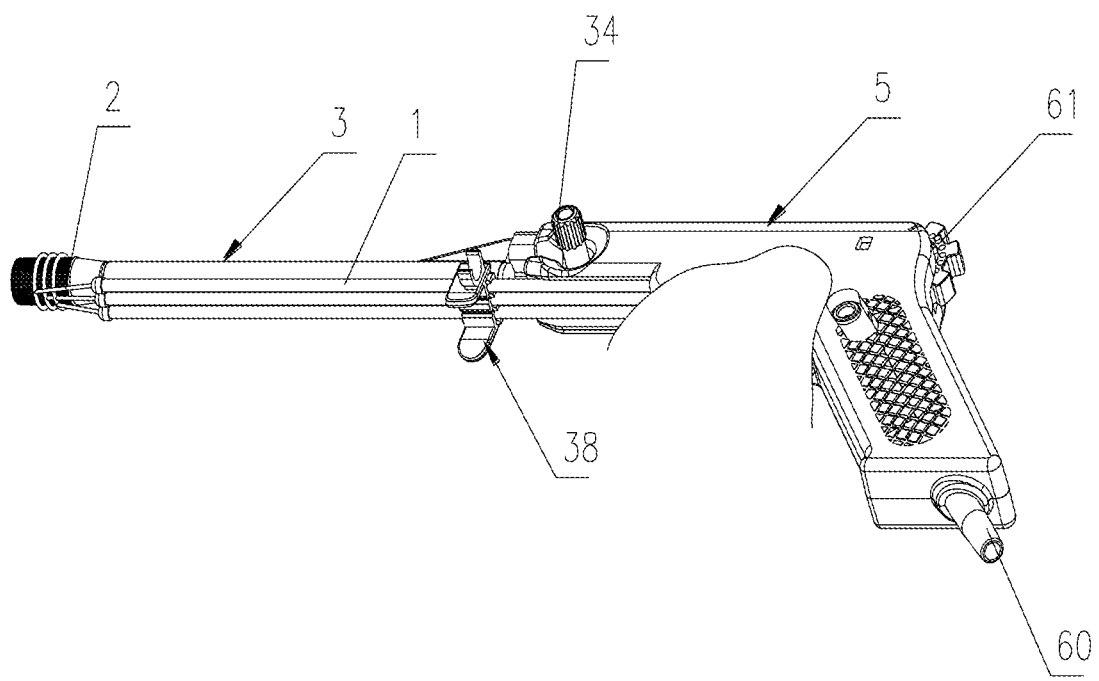
FIG. 12 is a schematic diagram (a facade is displayed) of a partial structure of embodiment 2 of the present invention.
Figure 13:
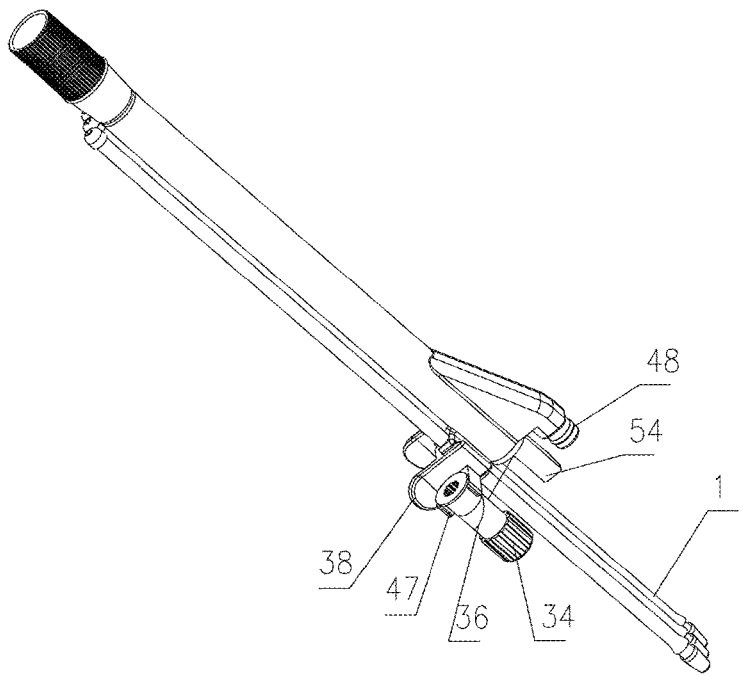
FIG. 13 is a first schematic diagram of a structure of a barrel in embodiment 2 of the present invention.
Figure 14:
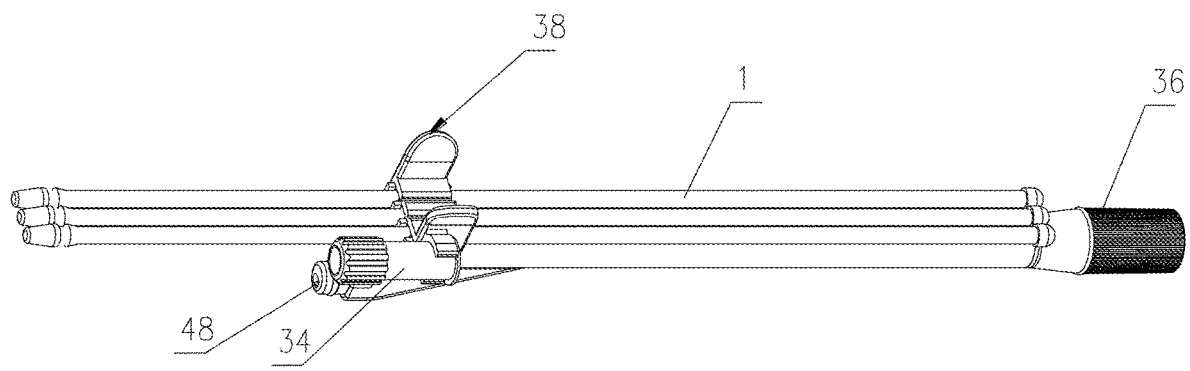
FIG. 14 is a second schematic diagram of a structure of the barrel in embodiment 2 of the present invention.
Figure 15:
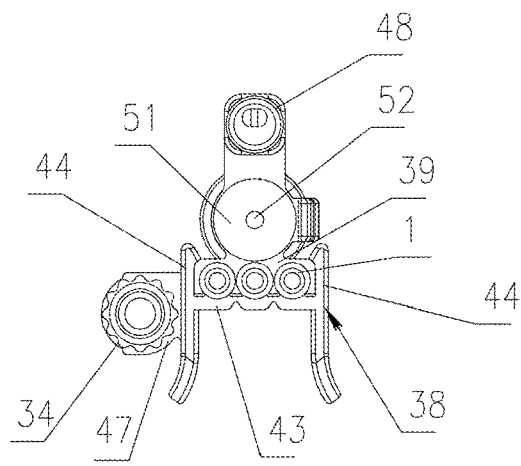
FIG. 15 is a rear view of the barrel in embodiment 2 of the present invention.
Figure 16:
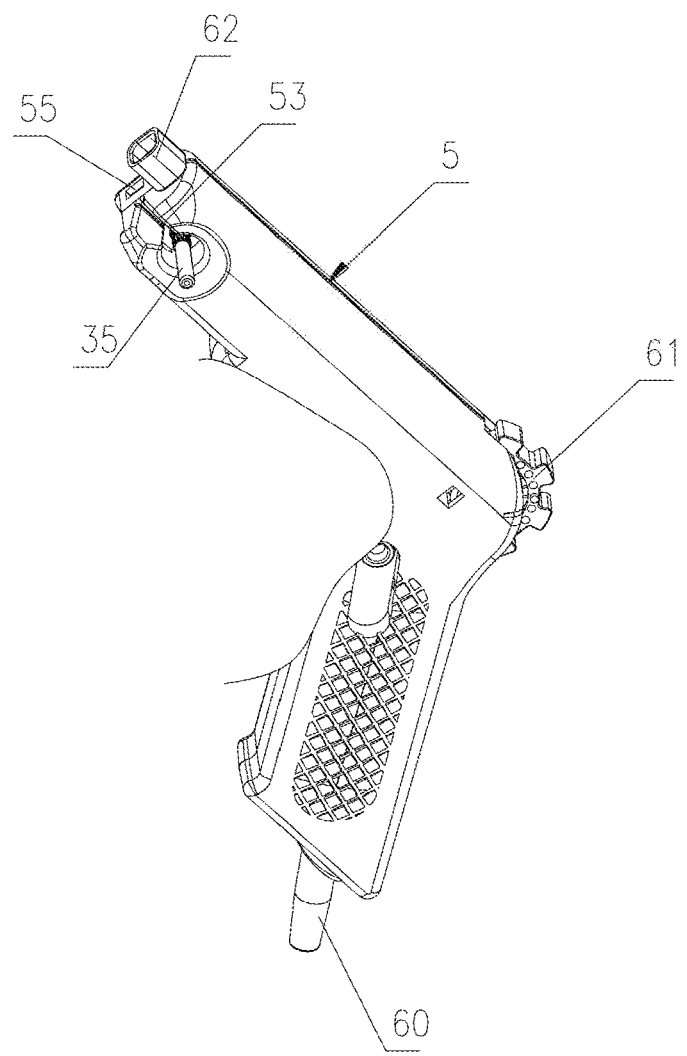
FIG. 16 is a schematic diagram of partial structures of the gun body and the stock in embodiment 2 of the present invention.
Figure 17:
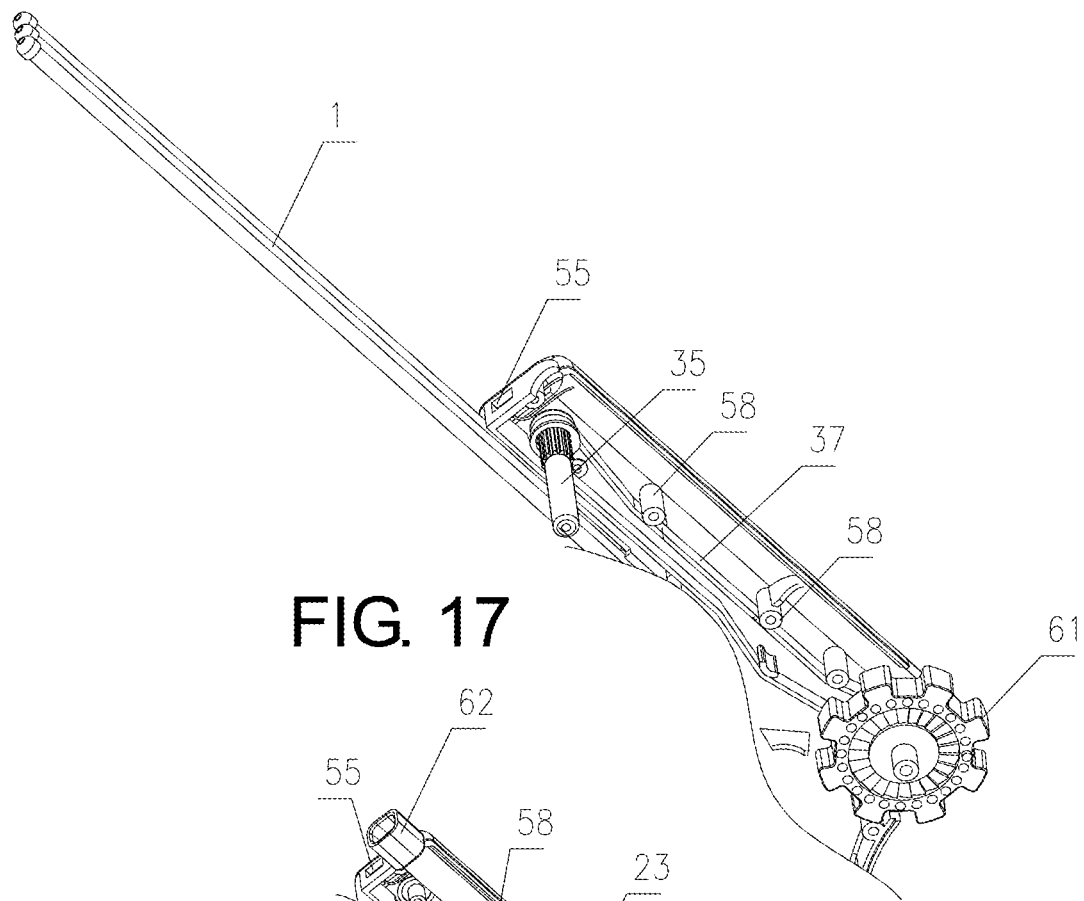
FIG. 17 is a schematic diagram of a partial structure of embodiment 2 of the present invention, after the thread ejector sleeve and a half shell of the gun body are detached.
Figure 18:
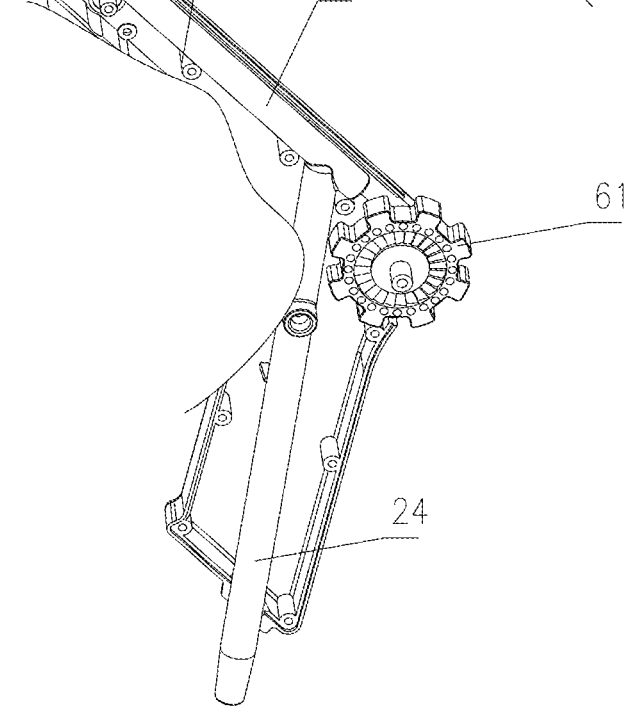
FIG. 18 is a schematic diagram of a partial structure of embodiment 2 of the present invention, after the half shell of the gun body is detached and a transmission belt and a transfer belt are removed.
Figure 22:
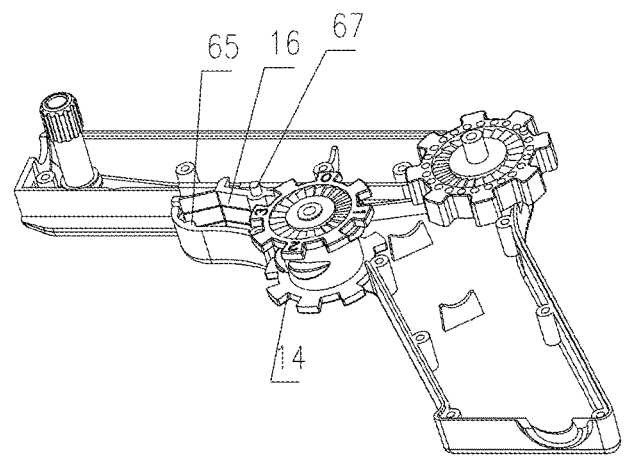
FIG. 22 is a second schematic diagram (no thread ejector sleeve is inserted) of a stereostructure of the thread ejector sleeve popup mechanism in embodiment 3 of the present invention.
Figure 23:
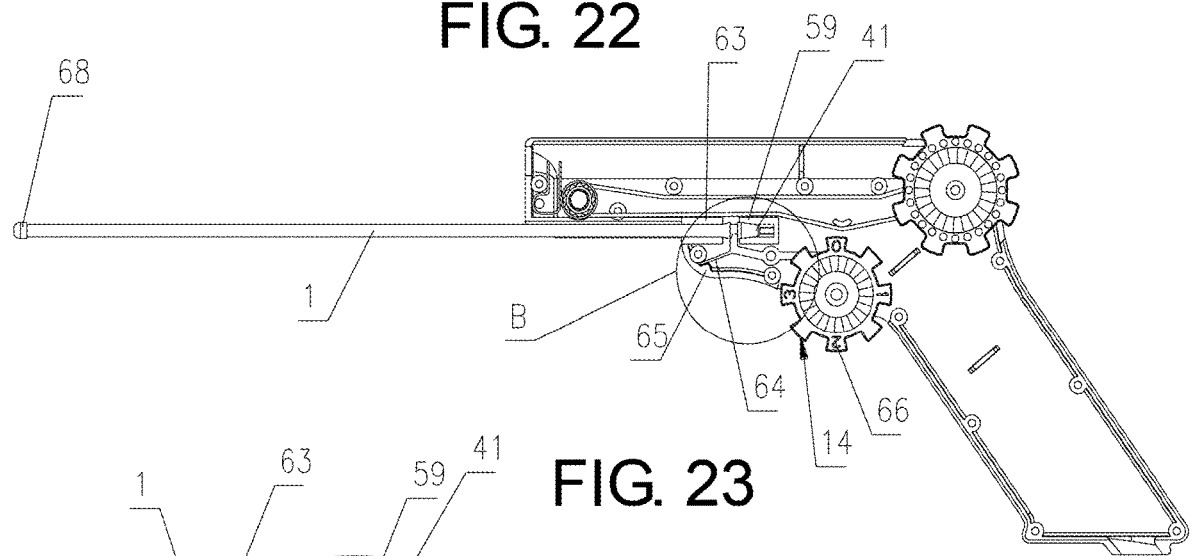
FIG. 23 is a first side view (the thread ejector sleeve is inserted, and it shows that a projection on a thread ejector sleeve release wheel does not lift a thread ejector sleeve lifting plate) of the thread ejector sleeve popup mechanism in embodiment 3 of the present invention.
Figure 24:
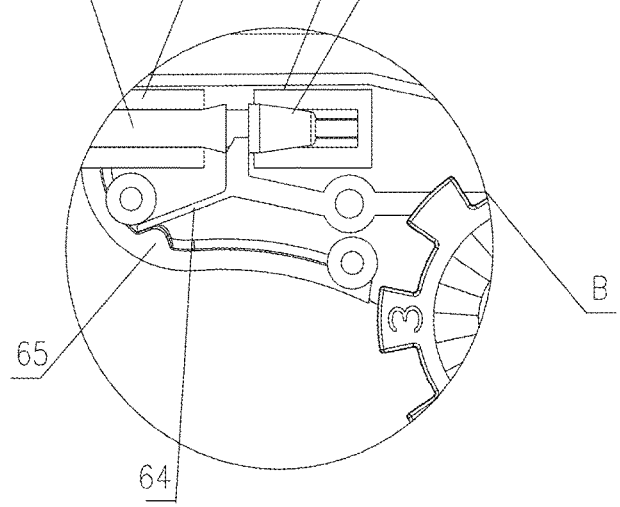
FIG. 24 is a B partial enlarged schematic diagram in FIG. 23.
Figure 25:
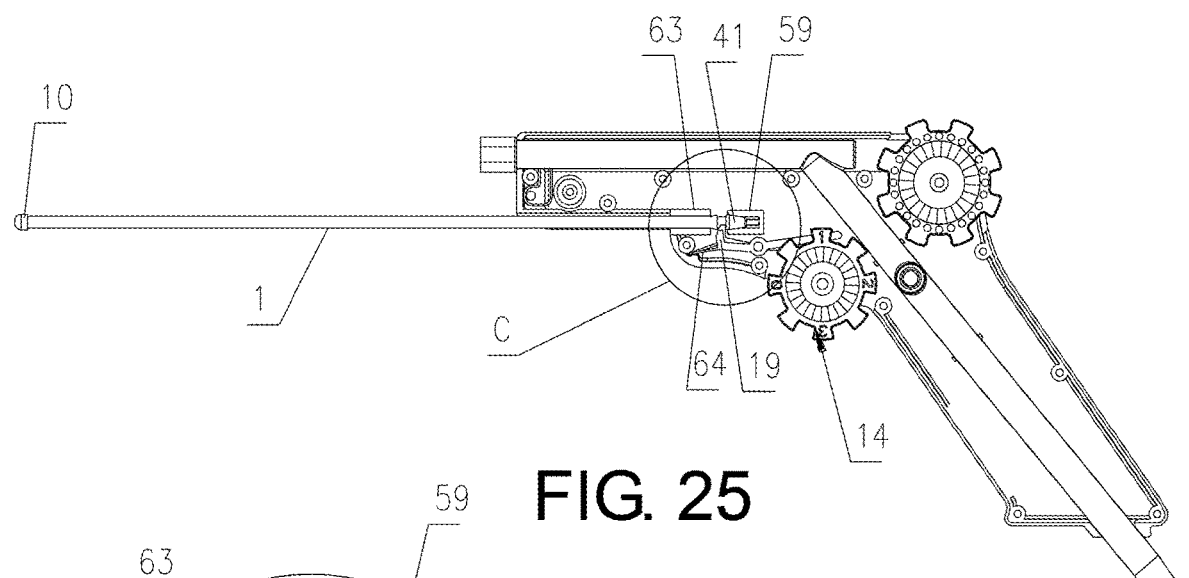
FIG. 25 is a second side view (the thread ejector sleeve is inserted, and it shows that the projection on the thread ejector sleeve release wheel lifts the thread ejector sleeve lifting plate) of the thread ejector sleeve popup mechanism in embodiment 3 of the present invention.
Figure 26:
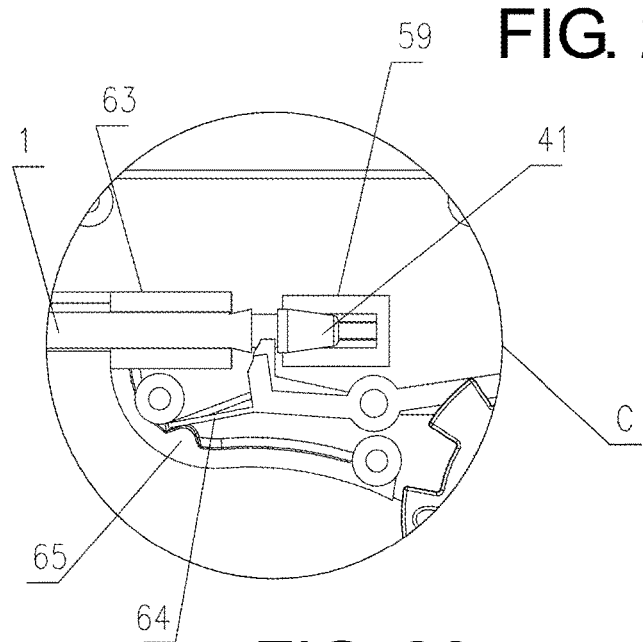
FIG. 26 is a C partial enlarged schematic diagram in FIG. 25.
Figure 27:
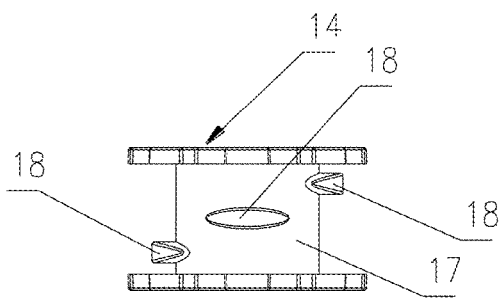
FIG. 27 is a top view of the thread ejector sleeve release wheel.
Figure 28:
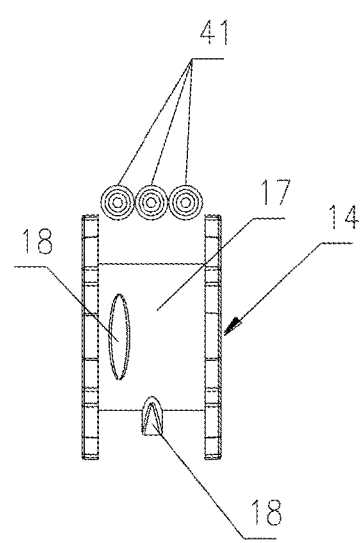
FIG. 28 is a schematic diagram of cooperation of the thread ejector sleeve release wheel and the thread ejector sleeve.
Figure 29:
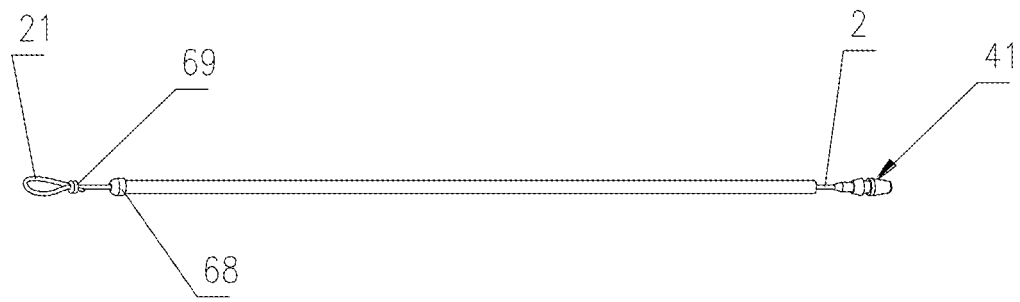
FIG. 29 is a first structure diagram of assembly of the thread ejector sleeve, an elastic thread and a clamping joint.
Figure 30:
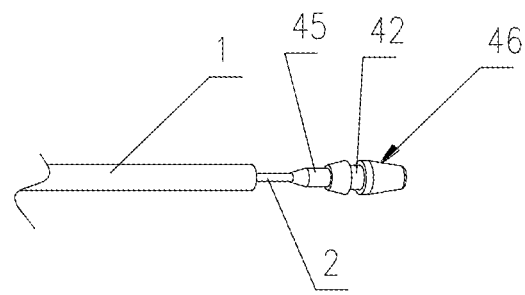
FIG. 30 is a schematic diagram of an enlarged structure of the clamping joint.
Figure 31:
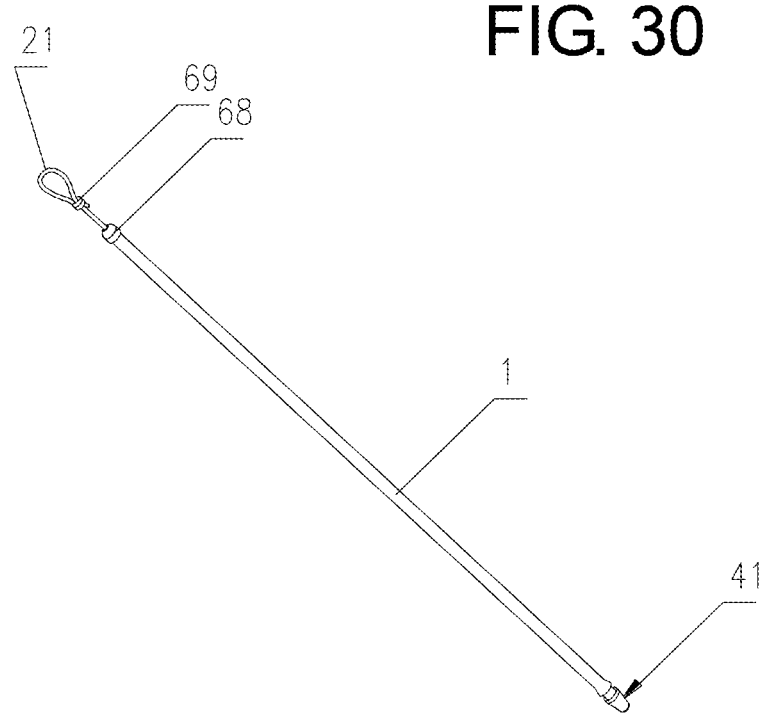
FIG. 31 is a second structure diagram of assembly of the thread ejector sleeve, the elastic thread and the clamping joint.

In other embodiments, as shown in FIG. 10, the annular sleeve 21 with the adjustable aperture and at the front end of the elastic thread 2 can also be formed by penetrating a thread fixing bead 27 through the elastic thread 2, and the thread fixing bead 27 is the force bearing part propping against the annular sleeve 21; specifically, the tail end of the elastic thread 2 penetrates through the thread ejector sleeve 1 and is knotted to the knot 28, the tail end of the elastic thread is buckled with the orifice at the rear end of the thread ejector sleeve 1, the front end of the elastic thread 2 penetrates through the orifice at the front end of the thread ejector sleeve and penetrates through a pore channel 29 of the thread fixing bead 27, a mechanism capable of clamping the elastic thread 2 is arranged in the pore channel 29 and only allows the elastic thread to be pulled in a single direction, and this mechanism can be achieved by the existing technical means; and then, the elastic thread 2 is folded back and penetrates through another pore channel 32 on the thread fixing bead to form a knot 33 so as to be clamped at the orifice of the pore channel 32.

A neck 11 is formed in the tail end of the thread ejector sleeve 1, and a shiftable clamping projection 7 is arranged in the neck 11 to position the thread ejector sleeve 1. Specifically, the neck 11 is formed in the rear of the thread ejector sleeve 1, and the rear of the thread ejector sleeve 1 penetrates through the inner cavity of a gun body 5; a slide rail 12 extending along the transverse direction is arranged on the inner wall of the gun body 5, a thread ejector sleeve release button 13 is installed on the slide rail 12 and can slide along the slide rail 12, and the clamping projection 7 on the thread ejector sleeve release button 13 is clamped in the neck 11 of the thread ejector sleeve 1 to position the thread ejector sleeve 1; the thread ejector sleeve release button 13 is pressed to deviate the clamping projection 7 from the neck 11, and at this time, the thread ejector sleeve 1 and the elastic thread 2 can be detached. The thread ejector sleeve release button 13 is composed of an elastic arm 8, a slide block 9 and a press panel 10; one end of the slide block 9 and the one end of the elastic arm 8 are respectively connected to the back surface of the press panel 10, and the slide block 9 is slidably installed on the slide rail 12, the clamping projection 7 is arranged on the top face of the slide block 9, the neck 11 of the thread ejector sleeve 1 corresponds to the clamping projection 7 downwards, the other end of the elastic arm 8 is used as the lower end of the elastic arm to be propped on the inner wall of the gun body 5, the original length of the elastic arm 8 is larger than the length of the slide block 9 to propel the press panel 10, so that when the elastic arm 8 is deformed, the slide block 9 moves along the slide rail 12 to disengage the clamping projection 7 from the neck 11; after the acting force is withdrawn, the thread ejector sleeve release button 13 resets.

The above-mentioned method can be used in medical instruments, an automatic elastic thread ligation device using the above-mentioned method for setting elastic threads includes a barrel 3, an emission head 31, a gun body 5, a stock 22, a traction thread, a reel 6 arranged at the rear in the gun body 5, a negative pressure joint 40 communicated with the barrel 3, at least one elastic thread 2, a thread ejector sleeve 1 and a negative pressure release switch 30 arranged on the side face of the stock; the above components of the ligation device are made from a medical high-molecular material; wherein the gun body 5 and the stock 22 are provided with shells which are connected into a whole, and each shell is composed of two half shells which are butted joint. The cross section of the elastic thread is a circle, with a diameter of 1.0-3.0 mm, and the elastic thread is composed of an inner layer and an outer layer; the inner layer (an elastic strip) is made from a strip-shaped special high-molecular material with high elasticity; the outer layer (a wrapping layer) is a netty woven layer, is wrapped on the surface of the inner layer, is made from the special high-molecular material and can expand with the stretching of the inner layer elastic strip. This special double-layer structure of the elastic thread not only ensures good elasticity, but also can bear strong axial tension without breaking, and when being sleeved on a target tissue, the annular sleeve of the elastic thread at the stretched state can be further tightened to decrease the aperture; in addition, the elastic thread is unlikely to age and fatigue, so that the service life is long, and the ligation effect can be improved.

The emission head 31 is installed at the front end of the barrel 3; the traction thread penetrates through the emission head 31, the barrel 3 and the interior of the gun body 5, the rear end thereof is winded on the reel 6 for positioning the rear end of the traction thread, and the front end thereof stretches out from the orifice of the emission head 31 and is folded back on the outer wall of the emission head 31; the traction thread is also made from the special medical high-molecular material and can bear strong axial tension without breaking; the thread ejector sleeve 1 is installed and arranged along the outer wall of the barrel 3, in the embodiment, three thread ejector sleeves are adopted are arranged side by side; the rear half part of the thread ejector sleeve 1 penetrates through a positioning pipe 50 in the gun body 5 and is installed in the gun body 5 through a thread ejector sleeve release mechanism; the elastic thread 2 penetrates through the thread ejector sleeve 1, and the tail end thereof is buckled with the orifice at the rear end of the thread ejector sleeve 1, the knot 28 is formed at the tail end of the elastic thread 2 to be clamped in the orifice at the rear end of the thread ejector sleeve 1, a fixture block can also be clamped in the orifice at the rear end of the thread ejector sleeve 1, the front end of the elastic thread 2 penetrates through the orifice at the front end of the thread ejector sleeve 1 and is slightly pulled to keep the same at the stretched state, then a slipknot is knotted to form the annular sleeve 21 with an adjustable aperture, and the annular sleeve is sleeved on the outer pipe wall of the emission head 31; a traction block clamped with the annular sleeve 21 is arranged on the front end of the traction thread, in the embodiment, the traction block is formed by knotting the traction thread per se, the traction thread is located between the annular sleeve 21 and the outer wall of the emission head 31, and the traction block is located behind the annular sleeve 21. When the reel 6 is rotated, the traction thread moves backwards to drive the traction thread and the traction block folded on the pipe wall of the emission head to move forwards along the pipe wall, and the traction block drives the annular sleeve 21 to move towards the orifice of the emission head 31 until the annular sleeve is disengaged from the orifice. In the embodiment, the traction thread is composed of a main traction thread and two branch traction threads 26, which are interconnected, the other end of the main traction thread is winded on the reel, the other ends of the branch traction threads 26 stretch out from the emission head 31 and are symmetrically distributed along the orifice of the emission head to provide a uniform tension to the annular sleeve 21, so as to smoothly disengage the annular sleeve 21 from the orifice of the emission head 31 and sleeve the annular sleeve on the target tissue.

In the embodiment, the thread ejector sleeve release mechanism includes three slide rails 12 and three thread ejector sleeve release buttons 13; the slide rail 12 is transversely arranged on the inner wall of the gun body 5 along the inner cavity of the gun body 5; the thread ejector sleeve release button 13 is slidably installed on the slide rail 12; a clamping projection 7 is arranged on the thread ejector sleeve release button 13, a neck 11 is formed in the rear of the thread ejector sleeve 1, and the clamping projection 7 is clamped in the neck 11; the arrangement positions (alternating along the transverse direction) of the clamping projections on the three thread ejector sleeve release buttons are different, and the clamping projection 7 on each thread ejector sleeve release button 13 is matched with one neck 11 on the thread ejector sleeve 1 on a corresponding position; for the convenience of production and installation, three necks 11 are formed in each thread ejector sleeve 1, namely, only the necks 11 corresponding to the clamping projections 7 on the thread ejector sleeve release buttons 13 are used. The thread ejector sleeve release button 13 is integrally made from a press panel 10, a rectangular elastic arm 8 and a slide block 9, one end of the slide block 9 and the one end of the elastic arm 8 are respectively connected to the back surface of the press panel 10, and the slide block is located above the elastic arm, convex edges are arranged on both sides of the slide block 9, a groove is formed in the slide rail 12, and the convex edges of the slide block 9 are located in the groove of the slide rail 12 to achieve the slide connection of the slide block and the slide rail; the clamping projection 7 is located on the top face of the slide block 9, the neck 11 of the thread ejector sleeve 1 corresponds to the clamping projection 7 downwards; the other end of the elastic arm 8 is used as the lower end of the elastic arm to be propped on the inner wall of the gun body 5, the original length of the elastic arm 8 is larger than the length of the slide block 9, and the press panel is located on the side face of the gun body for receiving a press force. Wherein, the elastic arm 8 is a bent sheet body, a convex limiting strip (not drawn in the figures) is arranged on the inner wall of the gun body 5 along the length direction thereof, the convex limiting strip is located below the elastic arm 8, and the rear end of the elastic arm 8 is clamped on the convex limiting strip. When no force is applied to the press panel 10, the elastic restoring force of the elastic arm jacks the clamping projection 7 in the neck 11; when the press panel 10 is pressed, the elastic arm 8 is compressed, meanwhile the convex limiting strip limits the rear end of the elastic arm 8, the slide block 9 moves along the slide rail 12 to disengage the clamping projection 7 from the neck 11, and at this time, the positioning of the thread ejector sleeve 1 is withdrawn; when the acting force is withdrawn, the thread ejector sleeve release button 13 resets.

A negative pressure pipeline is arranged in the gun body 5 and the stock 22, and the negative pressure pipeline is composed of a first negative pressure pipe 23 located in the gun body and a second negative pressure pipe 24 located in the stock, which are communicated; wherein the first negative pressure pipe 23 is communicated with the barrel 3, the reel 6 is located behind the first negative pressure pipe 23, and the traction thread is winded on the reel after being led out by the emission head 31, the barrel 3 and the first negative pressure pipe 23; a negative pressure release hole is formed in the second negative pressure pipe 24, and a plugging block used for plugging the negative pressure release hole is arranged on a negative pressure release switch 30; a negative pressure joint 40 is arranged at the tail end of the second negative pressure pipe 24, when a negative pressure suction system connected with the negative pressure joint 40 is opened, and the negative pressure release switch 30 is at a closed state, namely, the plugging block plugs the negative pressure release hole, the entire negative pressure pipeline, the barrel 3 and the inner cavity of the emission head 31 generate enough negative pressure to enable the opening end of the emission head 31 to suck the target tissue; after the ligation operation is finished, the negative pressure release switch 30 is opened to depart the plugging block from the negative pressure release hole, so as to eliminate the negative pressure in the pipeline to release the sucked target tissue.

It is taken as an example that the automatic elastic thread ligation device in embodiment 1 of the present invention is used as a medical instrument for ligating hemorrhoids tissues, the use working process thereof is as follows: the negative pressure joint is communicated with the negative pressure suction system at first, and the negative pressure release switch is closed; a handle is held by a hand to align the orifice of the emission head to the hemorrhoids tissue (or other target tissues); the negative pressure suction system is opened, and the hemorrhoids tissue is sucked into the orifice of the emission head; at this time, the reel is shifted by a finger to tow the traction thread to move backwards, under the action of a tractive force, the traction thread and the traction block distributed along the pipe wall of the emission head move towards the orifice of the emission head and drive the annular sleeve of the elastic thread to move towards the orifice until the annular sleeve is disengaged from the orifice of the emission head, and at this time, the hemorrhoids tissue is sleeved; the negative pressure release switch is opened to eliminate the negative pressure and release the ligated hemorrhoids tissue; the thread ejector sleeve release button is pressed to release the thread ejector sleeve, and the thread ejector sleeve is pulled out; a force is applied to the thread ejector sleeve to prop the orifice at the front end of the thread ejector sleeve against the knotting position of the annular sleeve and the hemorrhoids tissue at the position, and then the elastic thread at the orifice at the rear end of the thread ejector sleeve is pulled at the same time, the countertraction thereof further tightens the elastic thread and further decreases the aperture of the annular sleeve (at this time the aperture of the annular sleeve can be decreased to approximately zero), so as to further tighten the hemorrhoids tissue, and one ligation operation is finished. The next position is ligated with the same method, and ligation operations for three or more times can be continuously finished similarly.

Since the automatic elastic thread ligation device fastens and ligates the hemorrhoids tissue, after the hemorrhoids fall off, the ulcer surface is extremely small, so that the probability of postoperative bleeding of the ligation of hemorrhoids is reduced, and meanwhile, other inherent disadvantages (for example, rubber ring slippage occurs after a short period of the surgery to result in treatment failure; hemorrhoids block necrosis is incomplete to delay the healing of the ulcer surface, and the like) of the aforementioned rubber ring ligation are avoided.

When detecting the air tightness of the ligation device provided by the present invention, the negative pressure joint of the ligation device is connected to an external negative pressure suction system, meanwhile an exhaust vent switch is opened, the opening end of the emission head is plugged, and the negative pressure suction system is opened, and if the pointer of a negative pressure meter at least points to −0.08 MPa, the air tightness is qualified.

Embodiment 2

Embodiment 2 is a preferred embodiment of the present invention, and the main difference with embodiment 1 lies in that the barrel 3 is detachably installed on the gun body 5, a traction thread 36 is connected to a driving wheel 61 located at the rear of the gun body 5 through a transfer transmission mechanism, and when needing to pull the traction thread, the driving wheel 61 pulls backwards the traction thread through the transfer transmission mechanism (see FIG. 11 to FIG. 18). Meanwhile, the thread ejector sleeve is inserted into the gun body through a thread ejector sleeve popup mechanism (see FIG. 19 to FIG. 31).

In the embodiment, as shown in FIG. 11 to FIG. 18, the transfer transmission mechanism includes a traction thread turn button 34, a transfer shaft 35 and a transmission belt 37, wherein the transfer shaft 35 is transversely arranged at the front end in the gun body 5, the rear end of the transmission belt 37 is winded on the driving wheel 61 located at the rear in the gun body 5, the front end of the transmission belt 37 is sleeved on the inner end of the transfer shaft 35, the traction thread turn button 34 is sleeved on the outer end of the transfer shaft 35, the traction thread turn button 34 is engaged with the sleeving position of the transfer shaft 35, the rear end of the traction thread is winded on the front end of the traction thread turn button 34, the rear end of the traction thread turn button 34 stretches out from the gun body 5 to assemble and dissemble the same, the driving wheel 61 is shifted clockwise to drive the transfer shaft to rotate through the transmission belt, so that the traction thread turn button rotates for winding the thread to pull the traction thread backwards, so as to drive the annular sleeve to move towards the orifice of the barrel until the annular sleeve is disengaged from the orifice.

A buckling structure is arranged on the outer wall of the barrel 3, the buckling structure is composed of a thread ejector sleeve fixing clip 38 and at least one groove 39 formed in the outer wall of the barrel 3, the thread ejector sleeve fixing clip 38 is H-shaped, namely, the thread ejector sleeve fixing clip 38 is composed of a transverse plate 43 and a pair of vertical plates 44, the upper plate surface of the transverse plate 43 is provided with at least one bayonet, and the groove 39 corresponds to the bayonet up and down; necks are formed in both sides of the groove 39, a clamping hook is arranged at the upper end of the side plate of the thread ejector sleeve fixing clip 38, the clamping hook is clamped in the necks to install the thread ejector sleeve fixing clip 38 on the barrel 3, and the groove and the bayonet are oppositely closed to clamp the thread ejector sleeve so as to fix the thread ejector sleeve before the barrel is installed on the gun body. A C-shaped clamping opening 47 is formed in the outer wall of one vertical plate of the thread ejector sleeve fixing clip 38, the opening of the C-shaped clamping opening 47 is outward, and the traction thread turn button 34 is embedded into the C-shaped clamping opening 47 from the opening to be clamped, so as to fix the traction thread turn button before the barrel is installed on the gun body. In this way, the above-mentioned barrel, and the thread ejector sleeve, the elastic thread, the thread ejector sleeve fixing clip, the traction thread turn button and the traction thread and the like, which are arranged on the barrel, can be combined and assembled to a barrel assembly.

Two upper and lower parallel through holes are formed in the rear end of the barrel 3, the through hole at the upper side is a tubular plug 48, one end of a negative pressure pipeline 60 in the gun body 5 stretches out from the front end of the gun body 5 and is provided with a socket 62, and the plug 48 is hermetically inserted into the socket 62 to communicate the barrel 3 with the negative pressure pipeline 60, the negative pressure pipeline 60 is composed of a first negative pressure pipe 23 located in the gun body 5 and a second negative pressure pipe 24 located in the stock, which are communicated, the rear end of the first negative pressure pipe 23 is sealed, specifically: the plug 48 is communicated with the first negative pressure pipe 23, the driving wheel 61 is located behind the first negative pressure pipe 23, the first negative pressure pipe 23 is located above the transmission belt 37, and the negative pressure pipeline 60 is located on the side of the transmission belt. The through hole at the lower side is sealed by a rubber plug 51, a minipore 52 for enabling the traction thread to pass through is formed in the rubber plug 51, a wiring groove 53 communicated with an open bore enabling the traction thread turn button 34 to penetrate through is formed in the front end of the gun body 5, and the traction thread penetrates through the minipore 52 of the rubber plug 51 and extends straightly along the wiring groove 53 to be winded on the traction thread turn button 34. A tensioning column 58 used for tensioning the transmission belt 37 is arranged on the inner wall of the gun body 5, the tensioning column 58 is distributed on the peripheral side of the transmission belt 37, and the tensioning column 58 supports the transmission belt 37 to stably transmit power. Therefore, the negative pressure pipeline in the embodiment is completely separate from the wiring path of the traction thread.

A fixture block 54 with a clamping hook is arranged at the rear end of the barrel 3, a clamping hole 55 and a pushing element are arranged at the front end of the gun body 5, the clamping hole 55 is located on the front end face of the gun body 5 and is communicated with the interior of the gun body, the clamping hook of the fixture block 54 is clamped in the clamping hole 55, the pushing element is located on the side of the through hole at the lower side of the gun body, an open pore communicated with the interior of the gun body is formed in the side wall of the front end of the gun body 5, the pushing element is located in the open pore, the pushing element is composed of an elastic arm 56 and a push block 57 connected to the lower end of the elastic arm, the upper end of the elastic arm 56 is connected to the upper edge of the open pore to provide a restoring force to the push block 57, the push block 57 corresponds to the clamping hook of the fixture block 54, and the push block is pushed towards the interior of the gun body to enable the push block to shift the clamping hook to deviate the clamping hook from the clamping hole, so as to detachably insert the barrel assembly onto the gun body. In this way, by means of the above-mentioned structure on the rear end of the barrel, the barrel assembly can be conveniently detached from or installed on the gun body as a whole, and one gun body is collectively used with a plurality of barrel assemblies.

In the embodiment, as shown in FIG. 19 to FIG. 31, the thread ejector sleeve popup mechanism includes a thread ejector sleeve release wheel 14 arranged on the gun body and at least one strip-shaped thread ejector sleeve limiting plate 16, in the embodiment, three thread ejector sleeves 1 are arranged, are installed and arranged along the outer wall of the barrel 3 and are arranged side by side; correspondingly, three strip-shaped thread ejector sleeve limiting plates 16 are arranged, one thread ejector sleeve 1 is correspondingly clamped and limited at the front end part of each thread ejector sleeve limiting plate 16, the thread ejector sleeve release wheel 14 is rotatably installed at the lower part of the gun body 5, the three strip-shaped thread ejector sleeve limiting plates 16 are distributed in parallel along the longitudinal direction and are collectively hinged on the inner wall of the gun body 5 of the ligation device via the middle parts, at least one projection 18 used for prizing the thread ejector sleeve limiting plate 16 is alternately distributed on the wheel surface 17 of the thread ejector sleeve release wheel 14, in the embodiment, three projections 18 are arranged, the rotation of each projection 18 with the thread ejector sleeve release wheel 14 corresponds to one thread ejector sleeve limiting plate 16 located above the wheel surface, the thread ejector sleeve release wheel 14 is rotated to enable the projection 18 to lift the rear end part of the corresponding thread ejector sleeve limiting plate 16, so as to drive the thread ejector sleeve limiting plate 16 to rotate around a hinge shaft 67 thereof, meanwhile, the front end part of the thread ejector sleeve limiting plate 16 drops off to withdraw the limit on the thread ejector sleeve 1, and the thread ejector sleeve 1 pops up under the restoring force of the elastic thread 2. The front end of the elastic thread 2 is knotted into a slipknot to form the annular sleeve 21 with the adjustable aperture, the annular sleeve is sleeved on the emission head 31 of the automatic elastic thread ligation device, the front end head 68 of the popping out thread ejector sleeve can prop against the knotting position 69 of the elastic thread 2 to carry out a ligation operation.

A fixture block 19 is arranged at the front end part of the thread ejector sleeve limiting plate 16, a clamping joint 41 connected with the tail end of the elastic thread 2 is inserted into the orifice at the rear end of the thread ejector sleeve 1, a limiting groove 42 is formed on the clamping joint 41, and the fixture block 19 is clamped in the limiting groove 42 to limit the rear of the thread ejector sleeve 1 in the gun body 5. The clamping joint 41 is mainly composed of a columnar inner segment 45 inserted into the orifice at the rear end of the thread ejector sleeve 1 and an outer segment 46 stretching out from the thread ejector sleeve 1, the limiting groove 42 is annularly formed in the spindle-shaped outer segment 46, a neck 49 is formed in the upper end of the fixture block 19, the notch of the neck 49 is upward, the outline thereof is applicable to the outline of the bottom of the limiting groove 42, in the embodiment, the bottom of the limiting groove 42 is a cambered surface, the notch of the neck 49 is circular arc-shaped, and the neck is clamped in the limiting groove.

A lumpish rear supporting seat 59 used for being inserted into the outer segment of the clamping joint and a front supporting seat 63 used for guiding the thread ejector sleeve 1 to install the same in the gun body 5 of the ligation device can also be arranged, the two supporting seats are arranged on the inner wall of the gun body 5 at front and back, and the fixture block 19 of the thread ejector sleeve limiting plate 16 is located on the front side of the rear supporting seat 59. The rear of the thread ejector sleeve 1 stretches into the rear supporting seat 59 after penetrating through the front supporting seat 63. An elastic arm 64 obliquely extends from the lower side of the fixture block 19 at the front end part of the thread ejector sleeve limiting plate 16, the elastic arm 64 can form an included angle larger than 120 degrees with the thread ejector sleeve limiting plate 16, a longitudinal supporting column 65 is arranged in front of the elastic arm 64, the front end of the elastic arm 64 is propped on the supporting column 65 for providing an upward acting force to jack the fixture block 19 of the thread ejector sleeve limiting plate 16 in the limiting groove 42 of the clamping joint 41 and resetting the prized projection of the thread ejector sleeve limiting plate at the same time.

Markers 66 used for marking the thread ejector sleeves are arranged on the circumference of the side face of the thread ejector sleeve release wheel 14, the markers are numbers "0, 1, 2, 3", the marker "0" indicates that the rotating wheel is located at an original starting point, and the markers "1, 2, 3" respectively indicate that one projection on the wheel surface jacks the position of the rear end part of the corresponding thread ejector sleeve limiting plate, so as to master the popup conditions of the thread ejector sleeves.

See FIG. 20 to FIG. 24, they show that the projection 18 on the thread ejector sleeve release wheel 14 does not lift the thread ejector sleeve limiting plate 16, at this time, the marker "0" on the thread ejector sleeve release wheel 14 indicates that the thread ejector sleeve release wheel 14 is located at an original starting point, and no projection on the wheel surface 17 lifts the thread ejector sleeve limiting plate. See FIG. 25 and FIG. 26, the thread ejector sleeve release wheel 14 is rotated to make the projection 18 jack the corresponding thread ejector sleeve limiting plate 16, meanwhile, the elastic arm 64 of the thread ejector sleeve limiting plate 16 is propped on the supporting column 65 to deform, with the continuous rotation of the thread ejector sleeve release wheel 14, the acting force applied by the projection 18 to the thread ejector sleeve limiting plate 16 is withdrawn, the thread ejector sleeve limiting plate 16 resets through the elastic restoring force of the elastic arm 64, when the thread ejector sleeve is inserted, the elastic arm deforms, and when the limiting groove of the clamping joint corresponds to the fixture block of the thread ejector sleeve limiting plate (i.e., the thread ejector sleeve is installed in place), the fixture block of the thread ejector sleeve limiting plate is clamped in the limiting groove through the elastic restoring force of the elastic arm.

The use process of the embodiment is as follows: as shown in FIG. 19, a complete ligation device is assembled, when the thread ejector sleeve needs to pop up for ligation, the thread ejector sleeve fixing clip is taken off, the thread ejector sleeve release wheel is rotated from the position of the marker "0" to the position of the marker "1", one projection on the wheel surface lifts the rear end part of the corresponding thread ejector sleeve limiting plate, the thread ejector sleeve limiting plate is driven to rotate around the hinge shaft thereof, the front end part of the thread ejector sleeve limiting plate falls off to disengage the notch of the fixture block from the limiting groove, so as to withdraw the limit on the thread ejector sleeve, and the thread ejector sleeve is applied with the restoring force of the elastic thread at the stretched state, so that the rear end part of the thread ejector sleeve stretching in vivo pops up from the gun body. After the thread ejector sleeve pops up, the driving wheel is shifted by a finger to tow the traction thread to move backwards, under the action of the tractive force, the traction thread and the traction block distributed along the pipe wall of the emission head move towards the orifice of the emission head and drive the annular sleeve of the elastic thread to move towards the orifice until the annular sleeve is disengaged from the orifice of the emission head, and at this time, the hemorrhoids tissue is sleeved. At this time, a thread ejector sleeve assembly (including the thread ejector sleeve, the elastic thread, the annular sleeve at the head end of the elastic thread and the clamping joint at the tail end of the elastic thread) is completely dissociative. The front end of the dissociative thread ejector sleeve is propped against the force bearing part of the annular sleeve forwards, meanwhile, the clamping joint inserted into the orifice at the rear end of the thread ejector sleeve is pulled out from the columnar inner segment, so as to pull the traction thread backwards, and the countertraction between the two forces decreases the aperture of the annular sleeve gradually until the aperture becomes approximately zero, so as to firmly tighten the hemorrhoids tissue (or other target tissues); the negative pressure release switch is opened to eliminate the negative pressure and release the ligated hemorrhoids tissue from the emission head, and one ligation operation is finished. When the next thread ejector sleeve needs to pop up, the thread ejector sleeve release wheel is sequentially rotated to the positions of the markers "2, 3".

After the elastic threads of the above-mentioned barrel assembly are used up, and when needing to continue to use the elastic threads to carry out the ligation operation, the barrel assembly with the elastic threads used up can be detached; a new barrel assembly with elastic threads is installed on the gun body, meanwhile, the elastic threads penetrate through the front supporting seat to stretch into the gun body, in a stretching process, the outer segment of the clamping joint connected with the tail end of the elastic thread presses the fixture block to deform the elastic arm, the limiting groove of the clamping joint is clamped with the corresponding notch of the fixture block of the thread ejector sleeve limiting plate, the fixture block of the thread ejector sleeve limiting plate is clamped in the limiting groove by the elastic restoring force of the elastic arm, the tail end of the outer segment stretches into the rear supporting seat, and in this way, the thread ejector sleeve is installed in place. The traction thread turn button is sleeved on the transfer shaft, the thread ejector sleeve fixing clip is taken off, and then the above-mentioned ligation operation can be restarted.

Embodiment 3

The main difference of embodiment 3 over embodiment 1 lies in that the thread ejector sleeve is inserted into the gun body through a thread ejector sleeve popup mechanism, instead of the manner in embodiment 1 that the thread ejector sleeve is installed in the gun body through the thread ejector sleeve release mechanism. The specific composition, the connection relationship and the action process (see FIG. 20 to FIG. 31) of the thread ejector sleeve popup mechanism are the same as those of the thread ejector sleeve popup mechanism in embodiment 2, and will not be repeated redundantly herein. The ligation process in the embodiment is similar to that in embodiment 1, but only the operations of releasing the thread ejector sleeve are different.

In addition, a detachable installation structure of the barrel and the gun body in embodiment 2 can be combined into embodiment 1 to replace the integral connection of the barrel and the gun body in embodiment 1, and the ligation device (not shown in the figures) of another embodiment can be combined and connected to achieve the technical effects of the present invention as well.

The components in the embodiments of the above-mentioned ligation device can also be made from metals or other materials; at least two branch traction threads are arranged and are symmetrically distributed along the orifice of the emission head to provide a uniform tension to the annular sleeve of the elastic thread, so as to smoothly sleeve the annular sleeve on the target tissue; the connection between the traction thread and the annular sleeve can also be achieved in other manners; the tail end of the elastic thread penetrates through the thread ejector sleeve, and the tail end thereof can also be buckled with the orifice at the rear end of the thread ejector sleeve through the fixture block.

The embodiments of the present invention are not limited hereto, according to the above-mentioned contents of the present invention, in accordance with common technical knowledge and common means in the art, and on the premise of not departing from the above-mentioned basic technological ideas of the present invention, 1-3 or more thread ejector sleeves and elastic threads can be adopted in the present invention, and the matched components are correspondingly increased; the specific structures of the parts and components of the thread ejector sleeve popup mechanism of the automatic elastic thread ligation device provided by the present invention have other embodiments; the number of the thread ejector sleeve limiting plates and the projections on the thread ejector sleeve release wheel can be set according to the demand of the ligation device; therefore, a variety of other equivalent modifications, substitutions or combinations can also be made in the present invention, and these equivalent modifications, substitutions or combinations shall fall within the protection scope of the present invention.

What is claimed is:

1. A method for setting elastic threads in a ligation device, wherein at least one elastic thread is arranged along the outer wall of a barrel of the ligation device, and an annular sleeve with an adjustable aperture and formed at a front end of the elastic thread is sleeved on the outer wall of the front end of the barrel; a traction thread on the ligation device is connected with the annular sleeve of the elastic thread, and when the traction thread is pulled, the traction thread drives the annular sleeve to move towards an orifice of the barrel until the annular sleeve is disengaged from the orifice; a force bearing part of the annular sleeve at the front end of the elastic thread is propped forwards, meanwhile, a tail end of the elastic thread is pulled backwards, and countertraction between the two acting forces leads to a gradual decrease of the aperture of the annular sleeve at the front end of the elastic thread until the aperture of the annular sleeve becomes approximately zero.

2. The method of claim 1, wherein the annular sleeve with the adjustable aperture and at the front end of the elastic thread is formed by knotting a slipknot, and a knotting point of the annular sleeve is the force bearing part propping against the annular sleeve; or the annular sleeve with the adjustable aperture and at the front end of the elastic thread is formed by penetrating a thread fixing bead through the elastic thread, and the thread fixing bead is the force bearing part propping against the annular sleeve.

3. The method of claim 1, wherein a thread ejector sleeve is arranged on the elastic thread, and after the tail end of the elastic thread penetrates through the thread ejector sleeve, the tail end of the elastic thread is buckled with the orifice at the rear end of the thread ejector sleeve; a force is applied to the thread ejector sleeve to prop the orifice at the front end thereof against the force bearing part of the annular sleeve, meanwhile, the tail end of the elastic thread is pulled backwards, and the countertraction between the two forces leads to the gradual decrease of the aperture of the annular sleeve.

4. The method of claim 3, wherein a neck is formed in the tail end of the thread ejector sleeve, and a shiftable clamping projection is arranged in the neck to position the thread ejector sleeve.

5. An automatic elastic thread ligation device using the method of claim 1, comprising a barrel, a gun body and a traction thread, wherein the traction thread penetrates through the barrel and the rear end thereof is positioned in the gun body, the front end of the traction thread is folded back on the outer wall of the front end of the barrel after stretching out from the barrel; wherein the automatic elastic thread ligation device further comprises at least one elastic thread, the elastic thread is arranged along the outer wall of the barrel, an annular sleeve with an adjustable aperture and formed at the front end of the elastic thread is sleeved on the outer wall of the front end of the barrel, and the annular sleeve is connected with the front end of the traction thread; when the traction thread is pulled backwards, the traction thread drives the annular sleeve to move towards the orifice of the barrel until the annular sleeve is disengaged from the orifice; a force bearing part of the annular sleeve at the front end of the elastic thread is propped forwards, meanwhile, the tail end of the elastic thread is pulled backwards, and the countertraction between the two forces leads to a gradual decrease of the aperture of the annular sleeve until the aperture of the annular sleeve becomes approximately zero.

6. The automatic elastic thread ligation device of claim 5, wherein the automatic elastic thread ligation device further comprises a thread ejector sleeve used for propping against the force bearing part, one thread ejector sleeve is sleeved on each elastic thread, the tail end of the elastic thread penetrates through the thread ejector sleeve and is buckled with the orifice at the rear end of the thread ejector sleeve, and the rear of the thread ejector sleeve is inserted into the gun body.

7. The automatic elastic thread ligation device of claim 6, wherein the rear of the thread ejector sleeve is inserted into the gun body through a thread ejector sleeve release mechanism, the thread ejector sleeve release mechanism comprises a slide rail and a thread ejector sleeve release button, the slide rail is transversely arranged on the inner wall of the gun body along the inner cavity of the gun body, the thread ejector sleeve release button is slidably installed on the slide rail, and the thread ejector sleeve release button is exposed on the side face of the gun body, a clamping projection is arranged on the thread ejector sleeve release button, a neck is formed in the rear of the thread ejector sleeve, and the clamping projection is clamped in the neck to position the thread ejector sleeve.

8. The automatic elastic thread ligation device of claim 7, wherein the thread ejector sleeve release button is integrally made from a press panel, a rectangular elastic arm and a slide block, one end of the slide block and the one end of the elastic arm are respectively connected to the back surface of the press panel, and the slide block is located above the elastic arm, the slide block is slidably installed on the slide rail, the clamping projection is located on the top face of the slide block, the neck of the thread ejector sleeve corresponds to the clamping projection downwards, the other end of the elastic arm is used as the lower end of the elastic arm to be propped on the inner wall of the gun body, the original length of the elastic arm is larger than the length of the slide block, and the press panel is located on the side face of the gun body for receiving a press force.

9. The automatic elastic thread ligation device of claim 6, wherein the rear of the thread ejector sleeve is inserted into the gun body through a thread ejector sleeve popup mechanism, the thread ejector sleeve popup mechanism comprises a thread ejector sleeve release wheel and at least one strip-shaped thread ejector sleeve limiting plate, one thread ejector sleeve is correspondingly clamped and limited at the front end part of each thread ejector sleeve limiting plate, all the thread ejector sleeve limiting plates are arranged in parallel along the longitudinal direction and are collectively hinged on the inner wall of the gun body via the middle part; at least one projection used for prizing the thread ejector sleeve limiting plate is alternately distributed on the circumferential wheel surface of the thread ejector sleeve release wheel, the rotation of each projection with the thread ejector sleeve release wheel corresponds to one thread ejector sleeve limiting plate located above the wheel surface, the thread ejector sleeve release wheel is rotated to enable the projection to lift the rear end part of the corresponding thread ejector sleeve limiting plate, so as to drive the thread ejector sleeve limiting plate to rotate around a hinge shaft thereof, the front end part of the thread ejector sleeve limiting plate drops off to withdraw the limit on the thread ejector sleeve, and the thread ejector sleeve pops up under the restoring force of the elastic thread.

10. The automatic elastic thread ligation device of claim 9, wherein a fixture block is arranged at the front end part of the thread ejector sleeve limiting plate, a clamping joint connected with the tail end of the elastic thread is inserted into the orifice at the rear end of the thread ejector sleeve, a limiting groove is formed on the clamping joint, and the fixture block is clamped in the limiting groove.

11. The automatic elastic thread ligation device of claim 10, wherein the clamping joint is mainly composed of a columnar inner segment inserted into the orifice at the rear end of the thread ejector sleeve and an outer segment stretching out from the thread ejector sleeve, the limiting groove is annularly formed in the spindle-shaped outer segment, a neck is formed in the upper end of the fixture block, the notch of the neck is upward, the outline thereof is applicable to the outline of the bottom of the limiting groove, and the neck is clamped in the limiting groove.

12. The automatic elastic thread ligation device of claim 10, wherein the thread ejector sleeve popup mechanism further comprises a rear supporting seat used for being inserted into the outer segment of the clamping joint, and the fixture block is clamped in the limiting groove on the front side of the rear supporting seat.

13. The automatic elastic thread ligation device of claim 10, wherein an elastic arm obliquely extends from the lower side of the fixture block at the front end part of the thread ejector sleeve limiting plate, and the front end of the elastic arm is propped on a supporting column.

14. The automatic elastic thread ligation device of claim 9, wherein a marker used for marking the thread ejector sleeve is arranged on the circumference of the side face of the thread ejector sleeve release wheel, and the position of the marker corresponds to that of the projection.

15. The automatic elastic thread ligation device of claim 6, wherein the barrel is detachably inserted onto the gun body, the rear end of the traction thread is connected to a driving wheel located at the rear of the gun body through a transfer transmission mechanism, and the transfer transmission mechanism is driven by the driving wheel to pull the traction thread backwards.

16. The automatic elastic thread ligation device of claim 15, wherein the transfer transmission mechanism comprises a traction thread turn button, a transfer shaft and a transmission belt, wherein the transfer shaft is transversely arranged at the front end in the gun body, one end of the transmission belt is winded on the driving wheel, the other end of the transmission belt is sleeved on the inner end of the transfer shaft, the traction thread turn button is sleeved on the outer end of the transfer shaft, the traction thread turn button is engaged with the sleeving position of the transfer shaft, the rear end of the traction thread is winded on the traction thread turn button, the driving wheel is shifted to drive the transfer shaft to rotate through the transmission belt, so that the traction thread turn button rotates for winding the thread to pull the traction thread backwards, so as to drive the annular sleeve to move towards the orifice of the barrel until the annular sleeve is disengaged from the orifice.

17. The automatic elastic thread ligation device of claim 5, wherein the automatic elastic thread ligation device further comprises a reel, the reel is arranged at the rear in the gun body, and the rear end of the traction thread is winded on the reel for positioning the rear end of the traction thread.

18. The automatic elastic thread ligation device of claim 17, wherein the front end of the traction thread is located between the outer wall of the barrel and the annular sleeve, a traction block is arranged on the front end of the traction thread, and the traction block is located behind the annular sleeve for clamping the annular sleeve to connect the traction thread with the annular sleeve.

19. The automatic elastic thread ligation device of claim 18, wherein an emission head is installed at the front end of the barrel in the present invention, and the annular sleeve of the elastic thread is sleeved on the outer wall of the emission head; the traction thread is composed of a main traction thread and at least two branch traction threads, which are interconnected, the other end of the main traction thread is winded on the reel, the other end of each branch traction thread is folded back on the outer wall of the emission head after stretching out from the orifice of the emission head, and the branch traction threads are symmetrically distributed along the orifice of the emission head to provide a uniform tension to the annular sleeve of the elastic thread.

20. The automatic elastic thread ligation device of claim 5, wherein the elastic thread is formed by wrapping an elastic strip with a woven layer, both are made from a high-molecular material, and the woven layer can expand with the stretching of the elastic strip.

* * * * *